US010751452B2

(12) United States Patent
Topaz

(10) Patent No.: US 10,751,452 B2
(45) Date of Patent: Aug. 25, 2020

(54) WOUND HEALING DEVICE

(71) Applicant: Moris Topaz, Kibbutz Ramat Hacovesh (IL)

(72) Inventor: Moris Topaz, Kibbutz Ramat Hacovesh (IL)

(*) Notice: Subject to any disclaimer, the term of this patent is extended or adjusted under 35 U.S.C. 154(b) by 0 days.

(21) Appl. No.: 15/354,792

(22) Filed: Nov. 17, 2016

(65) Prior Publication Data
US 2017/0143881 A1 May 25, 2017

Related U.S. Application Data

(63) Continuation of application No. 12/993,776, filed as application No. PCT/IL2009/000500 on May 20, 2009, now abandoned.

(60) Provisional application No. 61/071,848, filed on May 21, 2008, provisional application No. 61/071,847, filed on May 21, 2008, provisional application No. 61/118,847, filed on Dec. 1, 2008.

(51) Int. Cl.
A61M 1/00 (2006.01)
A61M 35/00 (2006.01)
A61F 13/00 (2006.01)

(52) U.S. Cl.
CPC ..... *A61M 1/0084* (2013.01); *A61F 13/00029* (2013.01); *A61F 13/00038* (2013.01); *A61F 13/00068* (2013.01); *A61M 1/0025* (2014.02); *A61M 1/0031* (2013.01); *A61M 1/0037* (2013.01); *A61M 1/0088* (2013.01); *A61M 35/30* (2019.05); *A61F 2013/0017* (2013.01); *A61F 2013/00174* (2013.01); *A61M 2202/0208* (2013.01); *A61M 2205/15* (2013.01); *A61M 2205/33* (2013.01); *A61M 2205/3389* (2013.01); *A61M 2205/84* (2013.01)

(58) Field of Classification Search
CPC .. A61M 1/0088; A61M 27/00; A61M 1/0031; A61M 1/0023; A61M 1/0058; A61M 1/0084; A61M 2001/0027; A61M 2205/3344; A61M 1/0037; A61M 2001/0035; A61M 2205/3382; A61M 2039/0276; A61M 2202/0208; A61M 2205/3337; A61M 2205/3351; A61F 13/00068; A61F 2013/00536; A61F 2013/00174; A61F 2013/0054; A61F 13/0203
USPC .................................................. 604/543, 541
See application file for complete search history.

(56) References Cited

U.S. PATENT DOCUMENTS

| 4,915,691 A | 4/1990 | Jones et al. |
| 5,636,643 A * | 6/1997 | Argenta .............. A61M 1/0088 128/897 |
| 7,645,269 B2 | 1/2010 | Zamierowski |
| 2003/0212357 A1 | 11/2003 | Pace |
| 2004/0193218 A1 * | 9/2004 | Butler .................. A61N 5/0616 607/1 |
| 2006/0155260 A1 * | 7/2006 | Blott ................... A61M 1/0058 604/543 |

(Continued)

*Primary Examiner* — Andrew J Mensh
(74) *Attorney, Agent, or Firm* — Foley & Lardner LLP

(57) ABSTRACT

This invention provides wound healing systems, which delivers oxygen to the wound bed and applies negative pressure thereto, where the source of oxygen and negative pressure are simultaneously applied to distal sites of the dressing. Methods of treating wounds and methods of treating or preventing anaerobic infection of wounds using such systems are described.

20 Claims, 13 Drawing Sheets

(56) References Cited

U.S. PATENT DOCUMENTS

| | | | |
|---|---|---|---|
| 2006/0173253 A1* | 8/2006 | Ganapathy | A61B 5/0059 |
| | | | 600/310 |
| 2006/0287632 A1* | 12/2006 | Sarangapani | A61F 13/00068 |
| | | | 604/304 |
| 2007/0066946 A1* | 3/2007 | Haggstrom | A61M 1/0031 |
| | | | 604/313 |
| 2008/0103462 A1 | 5/2008 | Wenzel et al. | |
| 2008/0275409 A1* | 11/2008 | Kane | A61F 13/0203 |
| | | | 604/305 |
| 2011/0112492 A1* | 5/2011 | Bharti | A61M 1/0088 |
| | | | 604/319 |

* cited by examiner

1

WOUND HEALING DEVICE

FIELD OF THE INVENTION

This invention provides wound healing systems, which comprise dressings, which may be composed of at least two layers, which include a first absorptive and/or conductive and a second fluid impermeable layer and which system delivers oxygen to the wound bed and applies negative pressure thereto, where the source of oxygen and negative pressure are simultaneously applied to distal sites of the dressing. The system may comprise a fluid trap for collection of conveyed fluid and/or debris, which may further comprise a sensor for detection of changes in fluid volume or characteristics, a sensor to detect local pressure at the wound and distal limb, a controller to regulate differential vacuum levels and a means to regulate and synchronize application of negative pressure and oxygen. The invention is further directed to the application of oxygen and negative pressure wounds for use in treating such wounds, or treating or preventing anaerobic infection of such wounds.

BACKGROUND OF THE INVENTION

The treatment of open wounds that do not spontaneously close has long been a troublesome area of medical practice. These open wounds are a result of acute wounds, contaminated wounds, burns, extravasations and wound complications from failed surgery. Of those, necrotizing soft-tissue infections (NSTIs) are infrequent but highly lethal infections. They can be defined as infections of any of the layers within the soft tissue compartment (dermis, subcutaneous tissue, superficial fascia, deep fascia, or muscle) that are associated with necrotizing changes. Combinations of aerobes, anaerobes and facultative microbial agents often act synergistically to produce skin and soft tissue infections. The anaerobes proliferate in an environment of local tissue hypoxia in patients following trauma, surgery or medical compromise. Necrotizing fasciitis (NF) is a rapidly progressive inflammatory infection, spreading through the deep fascial plane, with secondary necrosis of the subcutaneous tissues. This deep infection causes vascular occlusion, ischemia, and tissue necrosis. Superficial nerves are damaged, producing the characteristic localized loss of sensation. Most necrotizing soft tissue infections have anaerobic bacteria present, usually in combination with aerobic gram-negative organisms. They proliferate in an environment of local tissue hypoxia in those patients with trauma, recent surgery, or medical compromise. Type 1 Necrotizing Fasciitis is a mixed infection caused by aerobic and anaerobic bacteria, and appears most commonly following surgical procedures and in patients with peripheral vascular disease (PVD) and diabetes. Type 2 Necrotizing Fasciitis refers to a mono-microbial infection caused mainly by group A *streptococcus* pyogenes. Pathogenesis of NF is rapid and can lead to loss of an associated limb or life.

Once the diagnosis of NF is confirmed, treatment should be initiated without delay. Several existing therapies such as early and aggressive surgical debridement and exploration of necrotic tissue, administration of systemic antibiotics, hyperbaric oxygen (HBO) and intravenous immunoglobulin are used with mixed success.

An ideal treatment for NF, in particular when the infection is caused by anaerobic bacteria, is unavailable and significant amputations and deaths result each year from NF.

SUMMARY OF THE INVENTION

In one embodiment, this invention provides a wound healing system comprising:

a dressing for wound containment;
a first inlet in said dressing, wherein said first inlet is operationally connected to a source for the application of negative pressure to a wound covered by said dressing; and
a second inlet in said dressing, wherein said second inlet is located distally to said first inlet and wherein said second inlet is operationally connected to a source for the application of oxygen flow, which conducts oxygen to a wound covered by said dressing.

In one embodiment, the wound healing system further comprises a fluid trap operationally connected to said first inlet, such that fluid from said wound fluid is conveyed to said trap, wherein said trap further comprises a detector moiety which senses a fluid level in said trap and regulates application of said negative pressure in response to achieving a defined fluid level or a change in fluid level, fluid characteristics, or a combination thereof.

In one embodiment, the wound healing system further comprises:

a first absorptive layer and a second impermeable layer; wherein said first layer is positioned proximal to said wound, and said second layer is distal to said wound and wherein said dressing is compartmentalized into sections, such that negative pressure is independently applied to each of said sections;
at least a second and third inlet operationally connected to a source for the application of negative pressure and operationally connected independently to said sections; whereby application of negative pressure to said dressing is unequal, such that a first portion of said dressing proximal to said second or third inlet is differentially subjected to negative pressure in comparison to a second portion of said dressing distal to said second or third inlet.

In some embodiments, the dressing comprises a second or third portion of the dressing, and in some embodiments, the dressing comprises a first impermeable layer a second absorptive layer and a third impermeable layer; wherein said first layer is positioned proximal to said skin, and said second layer is distal to said wound and wherein said dressing is compartmentalized into sections, such that negative pressure is independently applied to each of said sections; proximal or distal to the wound.

In one embodiment, this invention provides a method of treating a wound in a subject, said method comprising the steps of applying a source of oxygen containing to a wound in said subject and concurrently applying negative pressure to said wound, wherein said source of oxygen maintains wound atmospheric oxygen at a value of at least 21% of the total gas in said source and whereby application of oxygen and negative pressure to said wound stimulates wound healing.

In one embodiment, this invention provides a method of treating or preventing anaerobic infection of a wound in a subject, said method comprising the steps of applying a source of oxygen containing to a wound in said subject and concurrently applying negative pressure to said wound, wherein said source of oxygen maintains wound atmospheric oxygen at a value of at least 21% of the total gas in said source and whereby application of oxygen and negative pressure to said wound treats or prevents anaerobic infection of said wound.

In one embodiment, this invention provides a method of treating a wound in a subject, said method comprising:

applying the wound healing system of this invention to a wound in a subject such that said wound is substantially covered by said dressing;

applying negative pressure to said first inlet in said dressing; and concurrently or temporally applying oxygen to said second inlet;

whereby application of oxygen and negative pressure to said wound stimulates wound healing.

In one embodiment, this invention provides a method of preventing or treating a wound in a subject infected with or at risk for infection with an anaerobe, said method comprising:

applying the wound healing system of claim 1 to a wound in a subject at risk for or suffering from an anaerobic infection of said wound, such that said wound is substantially covered by said dressing;

applying negative pressure to said first inlet in said dressing; and concurrently or temporally applying oxygen to said second inlet;

whereby application of oxygen and negative pressure to said wound treats or prevents anaerobic infection of said wound or whereby application of oxygen and negative pressure to said wound stimulates wound healing.

In one embodiment, the methods of the invention further comprise the step of determining a blood pressure proximal to a body region containing said wound and applying said negative pressure to said inlet at a strength which is less than said blood pressure.

BRIEF DESCRIPTION OF THE DRAWINGS

Various embodiments of the subject wound healing system are described herein with reference to the figures wherein.

DETAILED DESCRIPTION OF THE INVENTION

Figure 1:
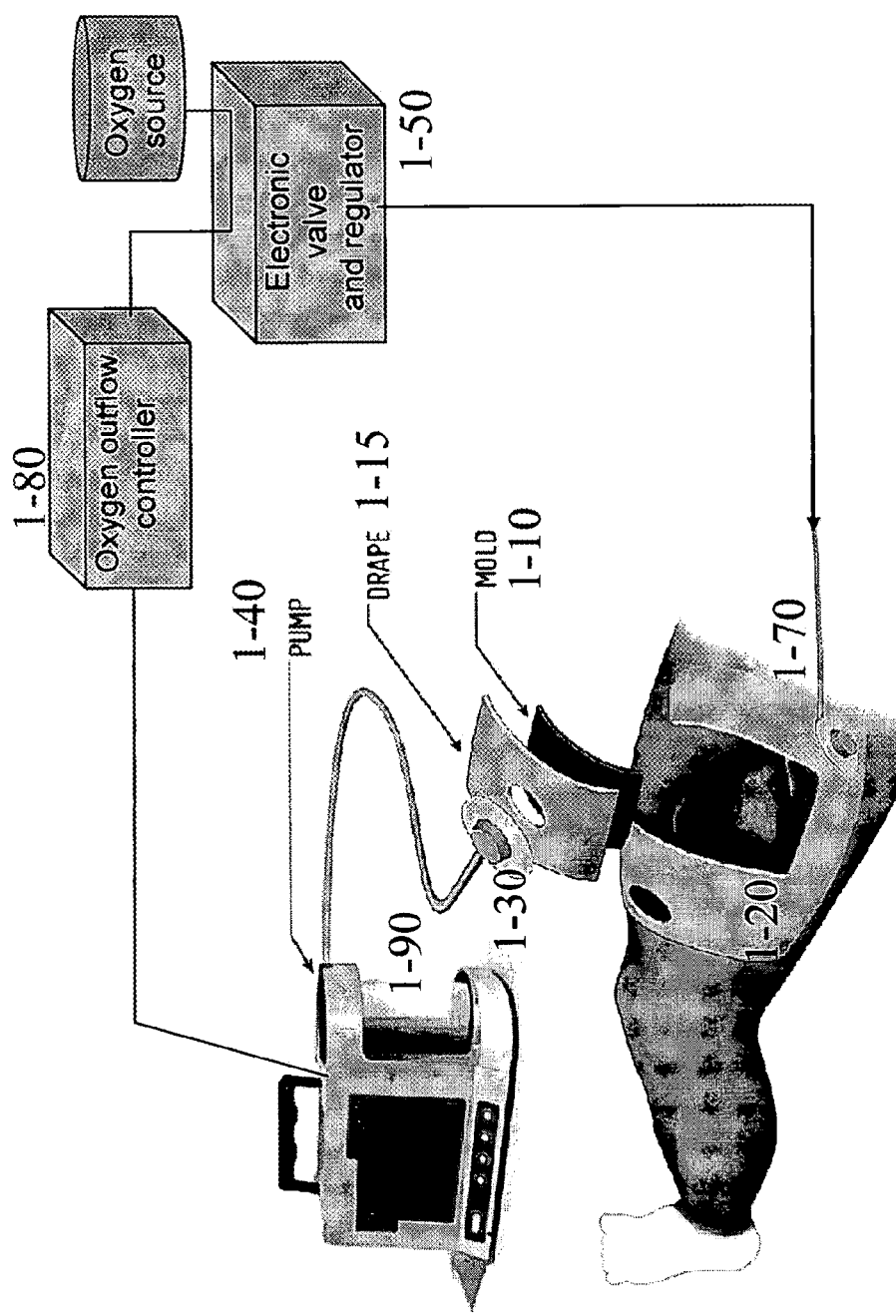
FIG. 1 depicts an embodiment of a wound healing system of this invention. The dressing (1-20), which may be comprised of a sponge mold (1-10) and a drape attached thereto (1-15) contains an inlet (1-30) through which negative pressure is applied (1-40) and another inlet (1-70) positioned distally thereto, through which oxygen is applied (1-50), whose delivery may be controlled by a valve and regulator system (1-50) and/or an oxygen outflow controller (1-80), which are operationally connected to the oxygen source (1-100). The source of negative pressure may in turn be operationally connected to a fluid trap (1-90).

This invention provides in one embodiment a system for wound healing comprising a dressing for wound containment, a first inlet in said dressing, wherein said first inlet is operationally connected to a source for the application of negative pressure to a wound covered by said dressing and a second inlet in said dressing, wherein said second inlet is located distally to said first inlet and wherein said second inlet is operationally connected to a source for the application of oxygen flow, which conducts oxygen to a wound covered by said dressing.

The wound healing systems of this invention reduce the risk of wound anaerobic infection, treat anaerobic infection and promote healing of a wound via the joint application of negative pressure and oxygen-enriched gas to the wound, wherein the negative pressure and oxygen application are applied at distal sites, with respect to each other. The wound healing system promotes the healing of the wound, in some embodiments, by application of oxygen enriched gas and negative pressure to defined segments in the dressing in sequential or intermittant manner. The wound healing system, in some embodiments, further comprises a fluid trap, having a sensor and relay system, such that upon changes in a fluid volume or spectroscopic properties in the fluid conveyed to the trap from the wound site, the relay system alters application of negative pressure, for example, decreasing application of negative pressure and oxygen, halting application of negative pressure and oxygen, or in some embodiments, increasing the application of negative pressure and oxygen.

In one embodiment, the dressing for wound containment further comprises a first absorptive layer and a second impermeable layer; wherein said first layer is positioned proximal to said wound, and said second layer is distal to said wound and wherein said dressing is compartmentalized into sections, such that negative pressure is independently applied to each of said sections; and at least a second and third inlet operationally connected to a source for the application of negative pressure and operationally connected independently to said sections; whereby application of negative pressure to said dressing is unequal, such that a first portion of said dressing proximal to said second or third inlet is differentially subjected to negative pressure in comparison to a second portion of said dressing distal to said second or third inlet.

This invention provides in another embodiment a system for wound healing as described hereinabove, further comprising at least third and fourth inlets for the application of regulated negative pressure, which are distal to the second inlet, through which oxygen is applied to the wound, and methods of use thereof.

In one embodiment, the term "dressing for wound containment" refers to any dressing or bandage or material, which serves as a barrier between the wound and the outside environment. The dressing fabric may be comprised of any suitable material, gas and fluid permeable, such as an ace bandage, stretch netting, or other clothing-type item made of a stretchable material, such as SPANDEX. The dressing, in some embodiments, has dimensions and composition such that it is suitable for the type and size of the wound, the location in the body in which the wound is located, the desired wound treatment, and the individual preference of the user of the dressing. In one embodiment, the dressing may comprise multiple layers which may vary in absorbance capacity creating a capillary action to facilitate flow of wound fluids from the wound. In some embodiments, the dressing is comprised of a material which absorbs wound fluids and provides a barrier to the outside environment over the entire, or primarily covering the wounded area. In some embodiments, the dressing will be compressible and elastic allowing the application of negative pressure and the covering of the wounded area. In some embodiments, the dressing is porous, which allows fluid drainage from the wound. In some embodiments, the application of the vacuum may vary in strength over a course of application to a dressing or to a dressing compartment. In some embodiments, the application of oxygen flow may vary over a course of application to a dressing or to a dressing compartment. Such application can be as a cycle, with repetitive variations in application in terms of vacuum strength and/or oxygen flow and in some embodiments, the pressure applied will be lower than the perfusion pressure detectable within the treated limb or body region.

In some embodiments, the dressing comprises a sponge, such as will be suitable for use with human skin lesions or wounds. The sponge, in some embodiments, is comprised of artificial polymeric materials or naturally available materials as long as they are suitable for use as dressing for wounds.

In some embodiments, the sponge is a combined layer sponge, where the first layer proximal to the wound is absorptive and the second layer distal to the wound is gas and fluid impermeable. The combined layer sponge may conform to the shape and size of the wound. In some embodiments, the combined layer sponge is connected to a negative pressure source through an inlet. The inlet may be attached to said combined layer sponge by conventional means such as adhesive, pressure application or screw application. In some embodiments, the dressing is comprised of materials which can be repeatedly sterilized, or in some embodiments, are sterile single-use materials. In some embodiments, the dressing will comprise suitable form, shape, etc., that conforms to the shape and size of the wound, and is appropriate for application thereto. In some embodiments, the sponge may vary in terms of pore diameter size or average pore volume, compressibility or cross link density. In some embodiments such differences in pore size and shape, etc., accommodate fluid drainage from the wound site. In some embodiments, the dressing is comprised of segments that are segregated from each other by a gas and fluid impermeable barrier. Each segment can be connected to a negative pressure source separately or in combination, resulting in application of negative pressure to part of or the whole dressing as determined by the treatment administrator. This allows the application of negative pressure in part of the dressing thus affecting part of the wound while differentially or not affecting a nearby part of the wound or body area where negative pressure is not needed. The segments, in one embodiment, may be in the form of a unit which has a plurality of annular compartments. Each compartment is connected to a negative pressure source for pressurizing the segment. In some embodiments, control valves are inserted between the pump and each dressing segment. Pressure sensors may be connected to each segment. The control valves and pressure sensors are connected to a programmable control processor to operate the valves and monitor the segment negative pressure thus enhancing blood and fluid flow in the limb and reducing the risk for deep vein thrombosis (DVT) and limb ischemia and facilitating limb perfusion, in some embodiments by avoiding excess negative pressure to the dressing.

In some embodiments, dressings may be changed over time, as a function of, for example, changes in healing dynamics of the wound. In some embodiments, for example, the sponge has a first pore size, and is optionally exchanged with a sponge having a second pore size, where the pore size is reduced as wound healing progresses. In some embodiments, the dressing may comprise materials whose mean pore size or pore volume density varies throughout the dressing. In some embodiments, the region of the dressing comprising a larger pore size is placed proximal to the wound to allow the fast flow and clearance of wound fluids and debris from the wounded area, and a region of the dressing comprising a smaller pore size is situated more distal to the wound site, and more proximal to the source of negative pressure. In some embodiments the reverse is effected, such that smaller pore size regions of the dressing are placed proximal to the wound area, in order that the wound is subjected to less adhesion of the sponge, whereas regions of the dressing comprising a larger pore size is placed distal to the wound site and proximal to the source of negative pressure to maximize application of pressure thereto and thereby stimulate effective wound drainage.

The term "negative pressure" as used herein is to be considered synonymous with the terms "vacuum" or "sub-atmospheric pressure".

In some embodiments, the dressing and inlets therein are so positioned or structured such that the application from the source of oxygen and source of negative pressure, via the inlets or tubing, for example, are oriented distally with respect to each other along a single Cartesian axis, for example along a horizontal axis of the dressing. In some embodiments, according to this aspect, when a dressing is placed over a wound, and the wound comprises an area from left to right along a horizontal axis, the oxygen source is proximal for example, at the right-most edge of the dressing whereas negative pressure is applied at the left-most edge of the dressing. In some embodiments, the source or sources of oxygen and source or sources of negative pressure are oriented distally with respect to each other along a different Cartesian axis. For example, and in one embodiment, the source of oxygen is a region of the dressing proximal to the wound and the source of negative pressure is at a region distal to the wound along all Cartesian axes, for example, along a horizontal axis the oxygen source is applied to the middle of the wound area, whereas negative pressure is applied along a z axis most distal to the region of applied oxygen. In some embodiments, such arrangement facilitates directing oxygen flow to the wound site, conveyed by the front created by application of negative pressure. In some embodiments, several inlets for the application of negative pressure are deposited along a Cartesian axis, each in a different separated segment of the dressing as describe above. In some embodiment, these inlets are connected to a negative pressure through a valve which controls the application of negative pressure to one or more inlets at the same time.

In some embodiments, the dressing comprises commercial dressing materials, for example, XEROFLO® by Kendall Corp, or any available sponge dressing, for example as commonly sold by commercial vendors, such as Johnson and Johnson® or Micromat® sold by Sion Misgav Am Israel.

In some embodiments, the dressing is transparent. In some embodiments, the dressing comprises a resilient, liquid absorbent, porous, polymer-based sponge. In some embodiments, the dressing comprises a sponge comprising a dispensable liquid which at least partially solidifies to a crystal-like arrangement defining hollow tubes to allow for exudate drainage. In some embodiments, the dressing comprises a sponge dispensed within the wound bed, which is potentially collapsible to expel air from the sponge channels allowing the drainage of fluids from the wounded area. In some embodiments, the sponge may be expandable sponge which is capable of absorbing fluid from a wound and maintain the wound bed moist. In some embodiments, the sponge or the covering drape may incorporate a printed pattern, where the pattern deforms upon application of negative pressure. This serves as a visual indicator for the presence of negative pressure. In some embodiments, the pattern may comprise a drawing or printed word or a combination of the two where a visual change in the drawing and/or printed word indicates application or loss of negative pressure. In some embodiments, the indicator for application of negative pressure may be a color change. Upon application of negative pressure, a color print on the dressing may change color due to a change in elasticity, shape or size of the dressing indicating the availability of negative pressure applied to the dressing. The hollow tubes or voids defined by the sponge in some embodiments, may also provide a means to conduct electricity, heat, cold, fluids, gases negative pressure and ultrasound enabling additional treatments to be administered or tests to be done in parallel to treating the wound. In some embodiments, the hollow conduits, tubes or voids may also provide a bioactive scaffold for tissue growth, one possibility is that sponge is biodegradable thus allowing tissue regeneration without the need for sponge removal, scaffold or tissue regeneration or structuring. In one embodiment, a thin film transparent top layer is secured about the wound area to enclose the wound and seal the wound from atmospheric gases and potential infecting microorganisms.

In some embodiments, the dressings comprise hydrogels, medicaments and slow release medicaments, which may treat the wound, promote healing and reduce pain associated with dressing changes or removal. In some embodiments, medicaments include, for example, antimicrobial agents, growth factors, degradative enzymes, antibiotics, analgesics, and the like. In one embodiment, the medicaments are an anti-infective agent. In one embodiment, the anti-infective agent is an antibiotic agent. In one embodiment beta-lactam antibiotics include but are not limited to penicillin, benzathine penicillin, benzylpenicillin, amoxicillin, procaine penicillin, dicloxacillin, amoxicillin, flucloxacillin, ampicillin, methicillin, azlocillin, carbenicillin, ticarcillin, mezlocillin, piperacillin, phenoxymethylpenicillin, co-amoxiclav, cephalosporin, cefalexin, cephalothin, cefazolin, cefaclor, cefuroxime, cefamandole, cefotetan, cefoxitin, cefliiaxone, cefotaxime, ceftazidime, cefepime, cefpirome, imipenem, meropenem, ertapenem, faropenem, monobactam, aztreonam, or carbapenem.

In some embodiments, the dressings as described hereinabove, with respect to the materials utilized in construction of the same, may be arranged as layers, which vary in terms of their absorptive capacity, and are arranged such that the least absorptive material is the outermost layer of the dressing, or vice versa. In some embodiments, the dressings specifically incorporate a material which is fluid-impermeable, such as, for example, a plastic or nylon thin layer or sheath, which prevents fluid exchange with the environment. Suitable material for the fluid-impermeable may be any conventional material, for example, plastic film paper product, metallic foil, laminates or any other material which will be impermeable to fluids.

In some embodiments, the dressings incorporate an antibiotic. In one embodiment the antibiotic is a tetracycline antibiotic. In one embodiment tetracycline antibiotics include but are not limited to tetracycline, chlortetracycline, demeclocycline, doxycycline, lymecycline, minocycline, or oxytetracycline.

In one embodiment the antibiotic is a macrolide antibiotic. In one embodiment macrolide antibiotics include but are not limited to erythromycin, azithromycin, oxithromycin, dirithromycin, clarithromycin, josamycin, oleandomycin, kitasamycin, spiramycin, tylosin/tylocine, troleandomycin, carbomycin, cethromycin, or telithromycin.

In one embodiment the antibiotic is an aminoglycoside antibiotic. In one embodiment, aminoglycoside antibiotics include but are not limited to gentamicin, tobramycin, faropenem, imipenem, kanamycin, neomycin, ertapenem, apramycin, paromomycin sulfate, streptomycin, or amikacin.

In one embodiment the antibiotic is a quinolone antibiotic. In one embodiment quinolone antibiotics include but are not limited to ciprofloxacin, norfloxacin, lomefloxacin, enoxacin, ofloxacin, ciprofloxacin, levofloxacin, sparfloxacin, gatifloxacin, moxifloxacin, trovafloxacin, or alatrofloxacin.

In one embodiment the antibiotic is a cyclic peptide antibiotic. In one embodiment cyclic peptide antibiotics include but are not limited to vancomycin, streptogramins, Microcin J25, Bacteriocin AS-48, RTD-1, or polymyxins.

In one embodiment the antibiotic is a lincosamide antibiotic. In one embodiment lincosamide antibiotics include but are not limited to clindamycin.

In one embodiment, the antibiotic is an oxazolidinone antibiotic. In one embodiment oxazolidinone antibiotics include but are not limited to linezolid, U-100592, DA-7867, AZD2563, or U-100766.

In one embodiment, the antibiotic is a sulfa antibiotic. In one embodiment, sulfa antibiotics include but are not limited to sulfisoxazole.

In one embodiment, the antibiotic is an antiseptic agent. In one embodiment, antiseptic agents include but are not limited to alcohols, chlorhexidine, chlorine, hexachlorophene, iodophors, chloroxylenol (PCMX), quaternary ammonium compounds, or triclosan.

In one embodiment, the antibiotic is an anti-tuberculosis agent. In one embodiment an anti-tuberculosis agents include but are not limited to ethambutol, rifabutin, isoniazid, rifampicin, pyrazinamide, or rifampin In one embodiment, the antibiotic is an antifungal agent. In one embodiment, antifungal agents include but are not limited to terbinafine, flucytosine, fluconazole, itraconazole, ketoconazole, ravuconazole, posaconazole, voriconazole, caspofungin, micafungin, v-echinocandin, amphotericin B, amphotericin B lipid complex (ABLC), amphotericin B colloidal dispersion (ABCD), liposomal amphotericin b (1-Amb), liposomal nystatin, or griseofulvin.

In one embodiment, the antibiotic is an antiprotozoal agent. In one embodiment the antiprotozoal agent is an antimalarial agent. In one embodiment, antimalarial agents include but are not limited to chloroquine, mefloquine, proguanil, pyrimethamine with dapsone, pyrimethamine with sulfadoxine, quinine, or primaquine. In one embodiment, the antiprotozoal agent is an amoebicide. In one embodiment, amoebicides include but are not limited to metronidazole, tinidazole, or diloxanide furoate. In one embodiment, the antiprotozoal agent is an antigiadial agent. In one embodiment, antigiadial agents include but are not limited to metronidazole, tinidazole, or mepacrine. In one embodiment, the antiprotozoal agent is a leishmanicide. In one embodiment, leishmanicides include but are not limited to sodium stibogluconate. In one embodiment, the antibiotic is an antihelmintic agent.

In one embodiment, the antibiotic is an antiviral agent. In one embodiment, antiviral agents include but are not limited to abacavir, acyclovir, amantadine, didanosine, emtricitabine, enfuvirtide, entecavir, lamivudine, nevirapine, oseltamivir, ribavirin, rimantadine, stavudine, valaciclovir, vidarabine, zalcitabine, or zidovudine. In one embodiment, the antiviral agent is a nucleotide analog reverse transcriptase inhibitor. In one embodiment, nucleotide analog reverse transcriptase inhibitors include but are not limited totenofovir or adefovir. In one embodiment, the antiviral agent is a protease inhibitor. In one embodiment, protease inhibitors include but are not limited to saquinavir, ritonavir, indinavir, nelfinavir, amprenavir, lopinavir, fosamprenavir, or tipranavir. In one embodiment, the antiviral agent is a fusion inhibitor such as enfuvirtide. In one embodiment, a combination of antiviral or antiretroviral agents is desired. In one embodiment, antiviral or antiretroviral agents or a combination thereof, further comprise hydroxyurea, resveratrol, grapefruit, ritonavir, leflunomide, or a combination thereof.

In one embodiment, the dressing incorporates a medicament having a therapeutic property. In some embodiments, the medicaments may comprise a growth factor such as epidermal growth factor (EGF), transforming growth factor-α (TGF-α), platelet derived growth factor (PDGF), fibroblast growth factors (FGFs) including acidic fibroblast growth factor (α-FGF) and basic fibroblast growth factor (β-FGF), transforming growth factor-β (TGF-β) and insulin like growth factors (IGF-1 and IGF-2), or any combination thereof.

In one embodiment, the medicaments may be local anesthetic agents. In one embodiment, local anesthetic agents include but are not limited to benzocaine, chloroprocaine, cocaine, procaine, bupivacaine, levobupivacaine, lidocaine, mepivacaine, prilocaine, or ropivacaine. In one embodiment, the medicaments may be a general anaesthetic agent. In one embodiment, general anesthetic agents include but are not limited to esflurane, sevoflurane, isoflurane, halothane, enflurane, methoxyflurane, xenon, propofol, etomidate, methohexital, midazolam, diazepamor, ketamine, thiopentone/thiopental, or lidocaine/prilocaine.

In one embodiment, the medicaments may be an analgesic agent. In some embodiments, analgesic agents include but are not limited to paracetamol or non-steroidal anti-inflammatory agent. In some embodiments, analgesic agents include opiates or morphinomimetics such as morphine, pethidine, oxycodone, hydrocodone, diamorphine, tramadol, or buprenorphine. In some embodiments, a combination of two or more analgesics is desired.

In one embodiment, the medicaments may be sedative agents. In one embodiment, the sedative agent is an antidepressant agent such as mirtazapine or trazodone. In one embodiment, the sedative agent is a barbiturate such as secobarbital, pentobarbital, or amobarbital. In one embodiment, the sedative agent is a benzodiazepine such as diazepam, clonazepam, alprazolam, temazepam, chlordiazepoxide, flunitrazepam, lorazepam, or clorazepate. In one embodiment, the sedative agent is an imidazopyridines such as zolpidem or alpidem. In one embodiment, the sedative agent is a Pyrazolopyrimidine such as zaleplon. In one embodiment, the sedative agent is an antihistamine such as diphenhydramine, dimenhydrinate, or doxylamine. In one embodiment, the sedative agent is an antipsychotic agent such as ziprasidone, risperidone, quetiapine, clozapine, prochlorperazine, perphenazine, loxapine, trifluoperazine, thiothixene, haloperidol, or fluphenazine. In one embodiment, the sedative agent is an herbal sedative such as valerian plant mandrake, or kava. In some embodiments, the sedative agent is eszopiclone, ramelteon, methaqualone, ethchlorvynol, chloral hydrate, meprobamate, glutethimide, methyprylon, gamma-hydroxybutyrate, ethyl alcohol, methyl trichloride, zopiclone, or diethyl ether.

In one embodiment, the medicaments are agents treating a wasting disease. In some embodiments, agents treating a wasting disease include but are not limited to corticosteroids, anabolic steroids, cannabinoids, metoclopramid, cisapride, medroxyprogesterone acetate, megestrol acetate, cyproheptadine, hydrazine sulfate, pentoxifylline, thalidomide, anticytokine antibodies, cytokine inhibitors, eicosapentaenoic acid, indomethacin, ibuprofen, melatonin, insulin, growth hormone, clenbuterol, porcine pancreas extract, IGF-1, IGF-1 analogue and secretagogue, myostatin analogue, proteasome inhibitor, testosterone, oxandrolone, enbrel, melanocortin 4 receptor agonist, or a combination thereof.

In one embodiment, the medicaments are antidiabetic agent. In one embodiment, the antidiabetic agent is a sulfonylurea. In one embodiment, sulfonylureas include but are not limited to tolbutamide, acetohexamide, tolazamide, chlorpropamide, glipizide, glyburide, glimepiride, or gliclazide. In one embodiment, the antidiabetic agent is a meglitinide. In one embodiment, meglitinides include but are not limited to prandin or nateglinide. In one embodiment, the antidiabetic agent is a biguanide. In one embodiment, biguanides include but are not limited to metformin. In one embodiment, the antidiabetic agent is a thiazolidinedione. In one embodiment, thiazolidinediones include but are not limited to rosiglitazone, pioglitazone, or troglitazone. In one embodiment, the antidiabetic agent is an alpha glucosidase inhibitor. In one embodiment, alpha glucosidase inhibitors include but are not limited to miglitol or acarbose. In one embodiment, the antidiabetic agent is PPARα/γ ligand, dipeptidylpeptidase 4 (DPP-4) inhibitor, SGLT (sodium-dependent glucose transporter 1) inhibitor, or FBPase (fructose 1,6-bisphosphatase) inhibitor. In one embodiment, the antidiabetic agent is insulin. In one embodiment, the insulin is rapid-acting insulin. In one embodiment, the insulin is short-acting insulin. In one embodiment, the insulin is intermediate-acting insulin. In one embodiment, the insulin is intermediate- and short-acting insulin mixtures. In one embodiment, the insulin is long-acting insulin. In one embodiment, the antidiabetic agents are inhibitors of fatty acid binding protein (aP2) such as those disclosed in U.S. Ser. No. 09/519,079 filed Mar. 6, 2000, glucagon-like peptide-1 (GLP-1), and dipeptidyl peptidase IV (DPP4) inhibitors such as those disclosed in WO 0168603, which are incorporated by reference.

In one embodiment, the medicaments are anti-inflammatory agents. In one embodiment, the anti-inflammatory agent is a non-steroidal anti-inflammatory agent. In one embodiment, the non-steroidal anti-inflammatory agent is a cox-1 inhibitor. In one embodiment, the non-steroidal anti-inflammatory agent is a cox-2 inhibitor. In one embodiment, the non-steroidal anti-inflammatory agent is a cox-1 and cox-2 inhibitor. In some embodiments, non-steroidal anti-inflammatory agents include but are not limited to aspirin, salsalate, diflunisal, ibuprofen, fenoprofen, flubiprofen, fenamate, ketoprofen, nabumetone, piroxicam, naproxen, diclofenac, indomethacin, sulindac, tolmetin, etodolac, ketorolac, oxaprozin, or celecoxib. In one embodiment, the anti-inflammatory agent is a steroidal anti-inflammatory agent. In one embodiment, the steroidal anti-inflammatory agent is a corticosteroid.

In one embodiment, the medicaments may comprise anti-toxins or other agents, which counteract poisons. In some embodiments, the medicaments may comprise anti-proliferative agents.

In some embodiments, the dressings of this invention may comprise any medicament as described herein, or any combination thereof, or other therapeutic compounds and combinations thereof, as will be appreciated by the skilled artisan. In some embodiments, this invention should be understood to encompass administering to a subject treated by the methods or with the systems of this invention any of the medicaments or other therapeutic compounds, as known in the art and as described herein, wherein such administration may be via any desired route, however such agent or medicament is not incorporated within the dressings, in this aspect of the invention, or in some embodiments, such medicaments are incorporated in the dressings, and nonetheless the subject is administered similar, identical or other medications via a route other than delivery through the dressing.

Those skilled in the art will recognize that in some embodiments the dressing can be formed into any suitable shape. In some embodiments, the dressing may be adhered to the wound site by application of an adhesive material to the dressing. In some embodiments, the adhesive allows for dressing adhesion to the tissue surrounding the wound bed skin, e.g., the periwound area, and be of a material acceptable for use on skin without contact deterioration (for example, the adhesive should be non-irritating and non-sensitizing). Adhesives include, for example, in some embodiments the ULTEC Hydrocolloid Dressing, by Kendall Corp., a division of TycoHealthcare.

In some embodiments, the dressing may incorporate a flexible material, e.g., resilient or elastomeric, that seals the dressing resulting in a closed impermeable seal in which negative pressure and oxygen may be administered to the wound and the wound is protected/insulated from atmospheric gases and infecting microorganisms. In some embodiments, for example, the dressing is a transparent dressing manufactured under the trademark Opsite® by Smith and Nephew. Opsite® is a transparent adhesive film material which provides a barrier to microbes and fluid containment. In some embodiments, the transparency provides a means for visual indication of the status of the wound dressing and more particularly, the status of the saturation level of the layers of the wound dressing allowing the treating physician to monitor and decided on the regimen for wound dressing replacements. In some embodiments the transparent material allows for the detection of serious malfunctions of the dressing such as excessive bleeding. The top layer further includes a negative pressure application inlet in fluid and gas communication with the interior of the wound dressing. In some embodiments, the inlet may be a separate component attached to the top layer and connected thereto by conventional means such as adhesive, pressure application catheter or screw application. In some embodiments, it may be integrally formed with the top layer as part of the manufactured layer. In one embodiment, the inlet may have a valve built therein, e.g., a one way valve, to permit exudates to flow in one direction only, i.e., away from the wound dressing toward the container and negative pressure source. In some embodiments, several inlets are deposited along the dressing for the application of negative pressure to specific parts of the wound dressing. In some embodiments the dressing contains an inlet which is operationally connected to a source of negative pressure, positioned near a region where fluid accumulates within the affected tissue, in some embodiments, as a consequence of gravity.

In some embodiments, it is further contemplated that the wound healing system may incorporate external means or applications to stimulate tissue growth and/or healing. For example, in one embodiment, an auxiliary treatment apparatus may be incorporated into the wound healing system to impart electrical or mechanical energy for the treatment of the tissue such as, for instance, directing electrical, thermal or vibratory energy on the wound area and/or introducing various drugs into the human body through the skin. In some embodiments, the auxiliary treatment apparatus may be incorporated into the dressing. In some embodiments, sensor types are also contemplated for incorporation into the wound dressing apparatus including for example, oxygen, pressure, chemical, microbial and/or temperature sensors. In some embodiments, the detection of oxygen adjacent to the wound area would assist the clinician in determining the status of wound healing while allowing the clinician to follow and adjust the exact concentration of the oxygen at the site of the wound. In one embodiment, a microbial sensor may allow the clinician to follow the progress of removal of microbial flora, especially anaerobic bacteria, from the wound site. In some embodiments, using a temperature sensor may indicate the presence of an elevated temperature that can be indicative of an infection. In some embodiments, pressure sensor use may indicate the circumferential and/or local pressure induced by the vacuum dressing as well as the perfusion pressure to the treated area. It is to be understood that the clinician applying the systems and devices of this invention may regulate the applied pressure, to ensure that the pressure is of a value below that of the peripheral pressure measured in an area adjacent to the wound area being treated, in order to optimize perfusion of the wound site and the distal limb.

In some embodiments, the negative pressure source may incorporate circuitry to communicate with a computer, e.g., a hand-held PALM® device through wireless means resulting in no need for wires and other restrictive connections between the wound dressing and the monitoring appliances allowing the patient more freedom of movement during treatment.

In some embodiments a standard vacuum line may be used for application of negative pressure. In some embodiments, negative pressure is achieved by use of a pump in a portable or desktop device. In some embodiments, an example for a standard vacuum line is a wall socket vacuum. In some embodiments, a pump applies a negative pressure in the range of 20-500 mmHg to the wound to effectively draw wound fluid or exudate or debris away from the wound bed while in other embodiments, the pressure can be higher, for example in a range of from 200-500 mmHg, to allow fast removal of hazardous fluids or materials, such as toxic materials, from the wounded area. In some embodiments, the negative pressure source may be any type of pump that maintains or draws adequate and therapeutic negative pressure levels. In some embodiments, such pump is biocompatible. In some embodiments the negative pressure level to be achieved is in a range between about 20 mmHg and about 500 mmHg. In some embodiments, the pump may be removable, reusable, and/or rechargeable consistent with the need for mobility of the patient and allowing fast changes to be made to the wound dressing. In one embodiment, the pump is of the diaphragmatic or peristaltic type or the like, in which the moving part(s) draw exudates out of the wound bed into the wound dressing by creating areas or zones of decreased pressure e.g., negative pressure zones within the wound dressing. In some embodiments, there is a gradient of negative pressure created. In one embodiment, the area of decreased pressure communicates with the wound bed to facilitate removal of the fluids therefrom and into the contact layer/sponge. In some embodiments, the pump may be actuated by any means known by those skilled in the art. One suitable example of a peristaltic pump, in some embodiments, is the Kangaroo PET Enternal Feeding Pump manufactured by Kendall Corp., a division of TycoHealthcare. In another embodiment, a suitable example of a peristaltic pump may be the model 101 V/R pmy MK2 manufactured by Watson Mario w LTD of England. In some embodiments, the peristaltic pump produces subatmospheric pressure ranging from about 20 mmHg to about 500 mmHg. For example, in one embodiment, a suitable diaphragm pump includes model NMP 850 KNDC manufactured by KNF Neuberger of Germany. Other suggested vendors for the supply of pumps are Fisher Scientific, Emerson, Techno Takatsuki Co., Ltd and xenamedical Pleupump MK II. In some embodiments, a battery operated source for negative pressure can be used to allow patient mobility during treatment.

The wound dressing includes an inlet for the application of negative pressure. In some embodiments, tubing is connected to this inlet and further connected to the source for application of negative pressure. In some embodiments, the inlet and tubing may be comprised of any suitable flexible, partially compressible or non compressible tubing material fabricated from elastomeric and/or polymeric materials. In some embodiments, the tubing is surrounded by or comprised of a sponge material, as described hereinabove, which in some embodiments, comprises an absorptive layer, or a soft flat silicone tube, which forms the lumen of such tubing so that material conveyed via the tubing is maintained therewithin, while the external face of the tubing, which is exposed to for example, the subject's skin, is non-permeable, non-absorptive, soft and unlikely to leak fluid or gas, and/or unlikely to create or exacerbate sores. In some embodiments, the tubing is comprised of a sponge lining the lumen, and the sponge is surrounded by a fluid-impermeable coating. In some embodiments, use of sponge-based tubing minimizes irritation to the skin, which is in proximal contact therewith. In some embodiments, the dressings of the invention comprise a silicone or silicone-based flat tube (small flat soft drain) contained within the sponge, for example, between layers of the sponge.

In some embodiments, the dressing comprises a sponge that is prefabricated and attached to a covering drape, as opposed to applying a covering drape over the sponge-based dressing.

In some embodiments, the inlet tubing maybe of variable length and size as required by the specific condition of the wound and the physical position of the patient. In some embodiments, the inlet tubing is releasably connected to the source of negative pressure, for example, a vacuum port through conventional means including a friction fit, bayonet coupling, snap fit or the like. In some embodiments, the inlet may be embedded within the dressing or attached by an adhesive to an opening in the dressing or pressure inserted to the dressing. In some embodiments, the inlet is comprised of a polymeric material suitable to withstand the application of negative pressure.

In some embodiments, a fluid trap may be disposed "in-line" between the negative pressure source and the wound dressing for the removal of the drained wound fluids and to avoid contamination of the negative pressure source. In some embodiments, the fluid trap may be any flexible disposable pouch or the like. In some embodiments, the fluid trap may be a non-flexible container. In some embodiments, the fluid trap may include a super absorbent material such as superabsorbent polymers (SAP), silica gel, sodium polyacrylate, potassium polyacrylamide and related compounds to consolidate or contain wound drainage or debris. In some embodiments, the fluid trap may include a super absorbent material placed in an absorptive container, for example, caged so that when a fluid level rises to the top of the container, the absorbent material will becomes a gel. In some embodiments, the fluid trap is transparent to permit viewing into the interior of the trap to assist the patient in determining the remaining capacity of the fluid trap and quality of exudates, or to determine the rate of drainage of the filling of the trap. In some embodiments, the fluid trap may include a means for sampling the wound exudates to allow continuous monitoring of the wound status. Prior art describing means for fluid sampling are described in U.S. Pat. Nos. 6,890,323, 5,125,414 6,056,731, US20070060872A1, US20060189926A1, US20080077096A1, US20080015425A and US20030073932A1.

In some embodiments, this invention provides a wound healing system comprising a dressing for wound containment;

a first inlet in said dressing, wherein said inlet is operationally connected to a source for the application of negative pressure;

a second inlet in said dressing, wherein said second inlet is located distally to said first inlet, and wherein said second inlet is operationally connected to a source for the application of oxygen flow; and a fluid trap operationally connected to said first inlet, such that fluid from said wound fluid is conveyed to said trap, wherein said trap further comprises a detector moiety which senses a fluid level in said trap and regulates application of said negative pressure and optionally oxygen flow in response to achieving a defined fluid level or a change in fluid characteristics.

In some embodiments the fluid trap has a sensor for detection of fluid level and fluid characteristics. In some embodiments, such sensor may be based on specific gravity, detecting changes therein over time. In one embodiment, a simple float having a specific gravity between those of the process fluid and the headspace vapor will float at the surface, accurately following its rising and fall. Floats work on the principle of placing a buoyant object with a specific gravity intermediate between those of the process fluid and the headspace vapor into the tank, then attaching a mechanical device to read out its position. The float sinks to the bottom of the headspace vapor and floats on top of the process fluid. The float may be connected to a switch which upon reaching the predetermined level alerts by light and/or sound and activate a relay for shutting down the negative pressure source and oxygen flow.

In some embodiments, the devices and methods of this invention employ use of a sensor, which detects blood perfusion in the affected limb.

In some embodiments, the sensor maybe a hydrostatic device. Examples of hydrostatic measurement devices are: displacers, bubblers, and differential-pressure transmitters. Displacers work on Archimedes' principle. A column of solid material (the displacer) is suspended in the vessel. The displacer's density is always greater than that of the process fluid, thus it will sink in the process fluid, and it must extend from the lowest level required to at least the highest level to be measured. As the process fluid level rises, the column displaces a volume of fluid equal to the column's cross-sectional area multiplied by the process fluid level on the displacer. A buoyant force equal to this displaced volume multiplied by the process fluid density pushes upward on the displacer, reducing the force needed to support it against the pull of gravity. The transducer, in the form of a relay, which is linked to the transmitter, monitors and relates this change in force to level.

In some embodiments a bubbler-type level sensor maybe used. A dip tube having its open end near the vessel bottom carries a purge gas (typically air, although an inert gas such as dry nitrogen may be used when there is danger of contamination of or an oxidative reaction with the process fluid) into the tank. As gas flows down to the dip tube's outlet, the pressure in the tube rises until it overcomes the hydrostatic pressure produced by the liquid level at the outlet. That pressure equals the process fluid's density multiplied by its depth from the end of the dip tube to the surface and is monitored by a pressure transducer connected to the tube.

In some embodiments the sensor may be of a differential pressure (DP) level sensor. The essential measurement is the difference between total pressure at the bottom of the tank (hydrostatic head pressure of the fluid plus static pressure in the vessel) and the static or head pressure in the vessel. As with the bubbler, the hydrostatic pressure difference equals the process fluid density multiplied by the height of fluid in the vessel. Usually such sensor uses atmospheric pressure as a reference. A vent at the top keeps the headspace pressure equal to atmospheric pressure.

In some embodiments, the fluid sensor may be in the form of load cells. A load cell or strain gauge device is essentially a mechanical support member or bracket equipped with one or more sensors that detect small distortions in the support member. As the force on the load cell changes, the bracket flexes slightly, causing output signal changes. Calibrated load cells have been made with force capacities ranging from fractional ounces to tons. To measure level, the load cell must be incorporated into the vessel's support structure. As process fluid fills the vessel, the force on the load cell increases. Previous knowledge of the vessel's geometry (specifically, its cross-sectional area) and the fluid's specific gravity, allows converting the load cell's known output into the fluid level.

In some embodiments the fluid level sensor maybe of a magnetic level gauge. They are similar to float devices, but they communicate the liquid surface location magnetically. The float, carrying a set of strong permanent magnets, rides in an auxiliary column (float chamber) attached to the vessel by means of two process connections. This column confines the float laterally so that it is always close to the chamber's side wall. As the float rides up and down with the fluid level, a magnetized shuttle or bar graph indication moves with it, showing the position of the float and thereby providing the level indication. The system can work only if the auxiliary column and chamber walls are made of nonmagnetic material.

Traps, flanges, and process connections can be made from engineered plastics such as Kynar or exotic alloys such as Hastelloy C-276. Special trap configurations can handle a variety of conditions including biological hazard waste which needs to autoclaved for sterilization. Numerous metals and alloys such as titanium, Incoloy, and Monel are available for varying combinations of high-temperature, high-pressure, low-specific-gravity, and corrosive-fluid applications. Current magnetic level gauges can also be outfitted with magnetostrictive and guided-wave radar transmitters to allow the gauge's local indication to be converted into 4-20 mA outputs that can be sent to a controller or control system. This conversion maybe beneficial for a relay to be connected to the source for application of negative pressure and optionally oxygen flow, controlling its operation.

In another embodiment, the sensor may be a capacitance transmitter. These devices operate on the fact that process fluids generally have dielectric constants, significantly different from that of air, which is very close to 1. Oils have dielectric constants from 1.8 to 5. Pure glycol is 37; aqueous solutions are between 50 and 80. This technology requires a change in capacitance that varies with the liquid level, created by either an insulated rod attached to the transmitter and the process fluid, or an uninsulated rod attached to the transmitter and either the vessel wall or a reference probe. As the fluid level rises and fills more of the space between the plates, the overall capacitance rises proportionately. An electronic circuit called a capacitance bridge measures the overall capacitance and provides a continuous level measurement.

A more advanced method of fluid level measurement, and representing an embodiment for use in the system and methods of this invention, is using time-of-flight (TOF) measurements to transduce the liquid level into a conventional output. These devices typically operate by measuring the distance between the liquid level and a reference point at a sensor or transmitter near the top of the vessel. The systems typically generate a pulse wave at the reference point, which travels through either the vapor space or a conductor, reflects off the liquid surface, and returns to a pickup at the reference point. An electronic timing circuit measures the total travel time. Dividing the travel time by twice the wave's speed gives the distance to the surface of the fluid. The technologies differ mainly in the kind of pulse used to make the measurement. Ultrasound, microwaves (radar), and light all have proven useful.

In one embodiment, the sensor maybe in the form of a magnetostrictive level transmitter. In a magnetostrictive system, the float carries a series of permanent magnets. A sensor wire is connected to a piezoceramic sensor at the transmitter and a tension fixture is attached to the opposite end of the sensor tube. The tube either runs through a hole in the center of the float or is adjacent to the float outside of a nonmagnetic float chamber. To locate the float, the transmitter sends a short current pulse down the sensor wire, setting up a magnetic field along its entire length. Simultaneously, a timing circuit is triggered ON. The field interacts immediately with the field generated by the magnets in the float. The overall effect is that during the brief time the current flows, a torsional force is produced in the wire, much like an ultrasonic vibration or wave. This force travels back to the piezoceramic sensor at a characteristic speed. When the sensor detects the torsional wave, it produces an electrical signal that notifies the timing circuit that the wave has arrived and stops the timing circuit. The timing circuit measures the time interval (TOF) between the start of the current pulse and the wave's arrival. From this information, the float's location is very precisely determined and presented as a level signal by the transmitter. Key advantages of this technology are that the signal speed is known and constant with process variables such as temperature and pressure, and the signal is not affected by foam, beam divergence, or false echoes. Another benefit is that the only moving part is the float that rides up and down with the fluid's surface.

In another embodiment, an ultrasonic level transmitter sensor may be incorporated in the systems/methods of this invention. Ultrasonic level sensors measure the distance between the transducer and the surface using the time required for an ultrasound pulse to travel from a transducer to the fluid surface and back (TOF).

In one embodiment the sensor can be part of a laser level transmitter. Designed for bulk solids, slurries, and opaque liquids such as dirty sumps, milk, wound and blood fluids, and liquid styrene, lasers operate on a principle very similar to that of ultrasonic level sensors. Instead of using the speed of sound to find the level, however, they use the speed of light. A laser transmitter at the top of a vessel fires a short pulse of light down to the process liquid surface, which reflects it back to the detector. A timing circuit measures the elapsed time (TOF) and calculates the distance. The key is that lasers have virtually no beam spread (0.2° beam divergence) and no false echoes. Lasers are precise, even in vapor and foam. They are ideal for use in vessels with numerous obstructions and can measure distances up to 1500 ft.

Another sensor type which may be incorporated in the systems/methods of this invention is the radar level transmitter. Through-air radar systems beam microwaves downward from either a horn or a rod antenna at the top of a vessel. The signal reflects off the fluid surface back to the antenna, and a timing circuit calculates the distance to the fluid level by measuring the round-trip time (TOF). In guided wave radar (GWR) systems a rigid probe or flexible cable antenna system guides the microwave down from the top of the tank to the liquid level and back to the transmitter. As with through-air radar, a change from a lower to a higher causes the reflection. Guided wave radar is 20× more efficient than through-air radar because the guide provides a more focused energy path. Moreover, these systems can be installed either vertically, or in some cases horizontally with the guide being bent up to 90° or angled, and provide a clear measurement signal. GWR exhibits most of the advantages and few of the liabilities of ultrasound, laser, and open-air radar systems. Radar's wave speed is largely unaffected by vapor space gas composition, temperature, or pressure. It works in a vacuum with no recalibration needed, and can measure through most foam layers. Confining the wave to follow a probe or cable eliminates beam-spread problems and false echoes from tank walls and structures.

In another embodiment, the fluid trap may be connected to a sensor which employs photometric or optical methods for detecting the presence of blood in wound fluid being drawn away from the wound by the negative pressure device. In some embodiments, LEDs in the 540/560/580/620/640/660 nm and 800 nm ranges are used as the emitters and a photo detector sensitive to the same range of wavelengths is used as the receptor. These solid state optical components are positioned across a flow stream of the wound fluid and measurements are taken of the absorption of the illuminating light in a manner that specifically identifies and quantifies the presence of blood in the fluid. Variations in the system include different structures to hold or contain the wound fluid while optical measurements are being made as well as different placements of the detection site. One objective common to each implementation of the various previous embodiments dealing with fluid sensing is to allow for either the activation of a caregiver or patient notification signal and/or the automatic modification or cessation of the OPT. In either case the detection system of the present invention is capable of providing a digital output signal suitable for triggering any of a number of different caregiver/patient notification signaling devices or suitable for modifying the OPT operation. A notification signal would be associated with the identification of a wound fluid blood content that exceeded a pre-set level (>30% as an example) indicative of an abnormal condition (excessive bleeding) in the wound. Different types of wounds would merit different settings in this regard as would differing stages of wound healing.

Alternately, in one embodiment, the detection system could generate a staged signal that provided more refined "instructions" to the OPT system being implemented. For example, a given wound fluid blood concentration level could trigger a reduction in the negative pressure level of the therapy without altogether ceasing the therapy. A greater concentration or a sudden change in concentration could instead trigger the cessation of the therapy in conjunction with a notification signal. Because there potentially exists a variety of OPT regimens, a variety of modifications to these regimens, as triggered by wound fluid blood concentration levels, are anticipated. The low voltage/low current connections to a microprocessor may be structured with anything from a simple electrical conductor bundle connected to a power source same as the negative pressure source. In the alternative, the low power electronics (LEDs and photo detector) of the device could be locally powered (as by an onboard battery) and a wireless signal communication could be structured between the detector device (acting essentially as a remote blood sensor) and the signal processing instrumentation containing the microprocessor which controls the application of negative pressure.

As a further alternate application of the system of the present invention, color responsive chemical sensors (Elisa or non-layered biosensors, for example) may be incorporated in any of the sensing methods described to monitor chemical species in the wound fluid. Such species might include cytokines, creatinine, urea, among other chemicals of interest to those clinicians guiding the normal healing process of the wound.

In some embodiments, the negative pressure system includes an internal self contained battery source, a pressure sensor or transducer to monitor pressure within the wound dressing, and self-contained regulation or control means. In some embodiments, the pressure sensor is disposed within the interior of the wound dressing and is in electrical connection with the control means through an electrical wiring. An example, in one embodiment, of a suitable pressure sensor is the Dynamic ICP Pressure Sensor of the Pressure Division of PCB Piezotronics, Inc. The pressure sensor would also provide information to assist in detecting a leak in the wound dressing. In some embodiments, the control means is incorporated within the pump housing of the pump. In some embodiments, the control means may incorporate a motor controller/driver including processing and drive software or circuitry to control or vary the drive voltage to the motor of the pump responsive to the pressure sensed by the pressure sensor and/or other operational parameters including operational time constraints etc. For example, in one embodiment, the motor controller/driver may be programmed to run only for a predetermined period of time after start-up. The output of the pump motor may be increased or decreased, or initiated or discontinued, as controlled by the control means. In some embodiments, the regulation or control means may also have an alarm such as a visual, audio or tactile sensory alarm (e.g., vibratory etc.) to indicate when specific conditions have been met (e.g., the desired negative pressure level, loss of negative pressure or leak). In some embodiments, an override switch may also be incorporated within the pump system to allow optionally for the initiation or termination of the operation of the pump as desired without input from the control means. In one embodiment, wireless means are also envisioned to operate the pump through the control means. In some embodiments, a regulator will be utilized, which specifically synchronizes between the oxygen supply to the wound site and the application of the vacuum. Fluids are drawn away from the wound bed and into the contact layer of the wound dressing. These fluids and/or exudates are removed from the contact layer under the negative pressure of the pump. The fluids are delivered through the inlet and outlet tubing to be collected within the fluid trap. In one embodiment, once the desired level of sub atmospheric pressure is achieved as detected by, e.g., a pressure sensor, the pressure sensor sends a signal to the control means. In one embodiment, the control means may either terminate operation of the pump or alternatively vary the speed or output (e.g., decrease) of the pump. In this negative pressure state, wound fluid and exudates are continually drawn into the contact layer. After a period of time, the wound dressing may lose its vacuum state as detected by the pressure sensor or detected visually. When the loss of a desired vacuum level is achieved, the pressure sensor sends a signal to the control means to activate or increase the output of the pump. The negative pressure source removes the fluid from the contact layer and reestablishes the vacuum state within the wound dressing. In one embodiment, the dressing is comprised from segments which allow the application of negative pressure to each one of the segments without affecting nearby segment. An advantage of such kind of method is that it facilitate the application of negative pressures against a patient's limb and in so doing promote venous return. This is important both in wound healing and in the prevention of deep venous thrombosis (DVT) which sometimes occurs in surgical patients when they are confined to bed. When a DVT occurs, the valves that are located within the veins of the limb can be damaged which in turn can cause stasis and high pressure in the veins. Patients who have this condition often have limb swelling (edema) and tissue breakdown (venous stasis ulcer) in the limb. In one embodiment, for example, the system delivers negative pressure through the tubing sets to a pair of segments on the dressing and after a predetermined time relieves the pressure and applies negative pressure to different segments. In some embodiments, the negative pressure system independently compresses one or more of the segments. Negative pressure may alternate between the segments on the dressing resulting in a predetermined sequential order for the application of negative pressure in a way that in some embodiments, increases venous blood return and lymph flow. It is understood that wound healing system can detect any combination of garments and number of segments therein connected to one or more ports. As indicated hereinabove, in the alternative, the negative pressure source may be initiated via the manual override switch when for e.g., that the fluid trap is seen to be full. In one embodiment, the source for the application of negative pressure maybe portable, battery operated and carried by the patient, which permits patient mobility.

In addition to applying a negative pressure the methods and system of this invention rely on the application of high oxygen partial pressure to the wound. In some embodiments, the oxygen source is tethered to a separate inlet positioned distally to the negative pressure inlets on the wound dressing and maybe portable as well. Oxygen from a suitable source such as a pressurized tank of oxygen or an in-line/wall socket is supplied to the dressing end via an oxygen feed line/tubing connected to a filter which is connected to an oxygen inlet in the dressing. In some embodiments, the tubing may be any suitable flexible tubing fabricated from elastomeric and/or polymeric materials. It may vary in size and shape as required for treatment of the wound. In some embodiments, the inlet maybe embedded within the dressing or attached by an adhesive to an opening in the dressing. In some embodiments, the inlet is comprised of a polymeric, oxygen non-reactive material suitable to withstand the pressure from the oxygen source. In some embodiments, a pressure reducing valve, manually/automatically controllable to adjust the pressure of oxygen and/or the flow of oxygen fed to the tube is disposed in the line. In some embodiments, a manually controlled on-off valve is connected in the line between the tank and the pressure reducing valve. In use, in one embodiment, for example the oxygen valve is opened, and the valve is adjusted until the needed oxygen flow is achieved. In one embodiment, continues or interrupted oxygen flow may be used in the healing process of the wound. Oxygen concentration at the range of 21 to 100 percent is administered to the wound at a rate of 0.25-25 L/min depending on the wound size and/or the source of the vacuum. Detection of oxygen concentration, allowing real-time adjustment of oxygen at the vicinity of the wound, can be done, in some embodiments, by using an oxygen sensor. In one embodiment, an example of an oxygen sensor is Nellcor™ Oximax Sensors™. In some embodiments, an automatic controlled valve is connected in the line between the tank and the pressure reducing valve. The automatic valve may be connected, in some embodiments, to a relay which is responsive to the amount of oxygen inside the dressing. In one embodiment, the relay receives oxygen concentration measurements from an oxygen sensor embedded in the wound dressing. In one embodiment, the relay serves as controller for oxygen levels within the dressing by adjusting the flow of oxygen through the automatic valve. In some embodiments, synchronization between oxygen flow and actual vacuum in the wound is controlled by computerized predetermined control system.

In some embodiments, other potentially healing beneficial gases such as ozone maybe administered at a concentration ranging from 10 microgram/ml (0.21 micromol/ml) up to 80 microgram/ml (1.68 micromol/ml) in the patient blood. In some embodiments, the other beneficial gases maybe administered instead or in parallel to oxygen through the oxygen inlet by replacing the oxygen source with a different gas source. In some embodiments, other various gases available in the atmosphere, in different concentrations, may be used in treatment of the wound.

In one embodiment, the wound healing system includes an electric and or mechanical synchronizing control means to regulate simultaneous or consecutive application of vacuum and oxygen. Prior art describing regulated gas flow control are described in U.S. Pat. Nos. 4,651,729, 6,173,735, EP1396774B1, US20040099270A1, U.S. Pat. No. 6,647,982, 6,189,531. This control system receives signals from the pressure sensor and the oxygen sensor and regulates the flow of oxygen in accordance to conditions determined by the treatment administrator. This control allows monitoring, regulation and setting the concentration of oxygen in the wound. For example, oxygen should be regulated in parallel to the application of negative pressure to avoid over inflating the wound dressing with oxygen which may result in the concomitant separation of the covering top layer and loss of vacuum.

In some embodiments, both the negative pressure pump and the oxygen tank maybe of a portable type where the patient does not need to be constrained for any period of time during therapy and while exudates are being removed from the wound.

Referring now to FIG. 1, the wound dressing system in accordance with an embodiment of the present disclosure is illustrated herein. The wound dressing system includes a composite wound dressing 1-20, comprising an absorptive layer and a fluid impermeable layer, a negative pressure source (1-40) connected to the wound dressing by an inlet and tubing 1-30 and an oxygen source (1-60) connected to the wound dressing by an inlet and tubing 1-70, which source may additionally comprise a valve and regulator (1-50), an outflow controller (1-80), etc. to allow for regulated flow. This system allows the application of negative pressure in parallel to an inflow of oxygen. Moreover, in some embodiments, the oxygen inflow and negative pressure maybe constant, intermittent or independent one from the other. In one embodiment, a fluid trap 1-90 is operationally connected to a drainage source or tubing conveying fluid from the wound via the negative pressure inlet 1-30 to the negative pressure source 1-40 in order to collect fluids drown from the wound. The dressing 1-20 may comprise a first layer, which may also be referred to as the mold (1-10), and a covering drape (1-15), which may be adhered to the mold, or placed over the mold to form the dressing.

Figure 2A:
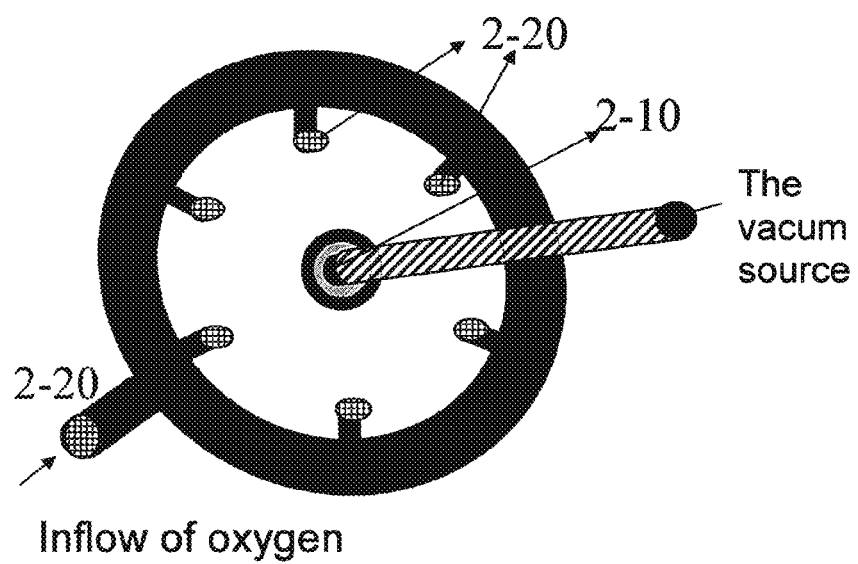
FIG. 2A is a cross-sectional view of an embodied wound healing system of the invention, illustrating the vacuum source operationally connected to an inlet (2-10), in this embodiment, via tubing, and an oxygen source operationally connected to a dressing inlet (2-20), which in turn may branch into multiple oxygen inlets positioned along the wound dressing.

In FIG. 2A, one embodiment of a cross section of the dressing is shown where inlets for application of negative pressure and oxygen (2-10 and 2-20 respectively) are positioned distally with relation of one to another. It is to be understood that the dressing may comprise multiple inlets for introduction of oxygen, as shown in the figure, and/or for applying negative pressure, and any such arrangement is to be considered as part of this invention.

Figure 2B:
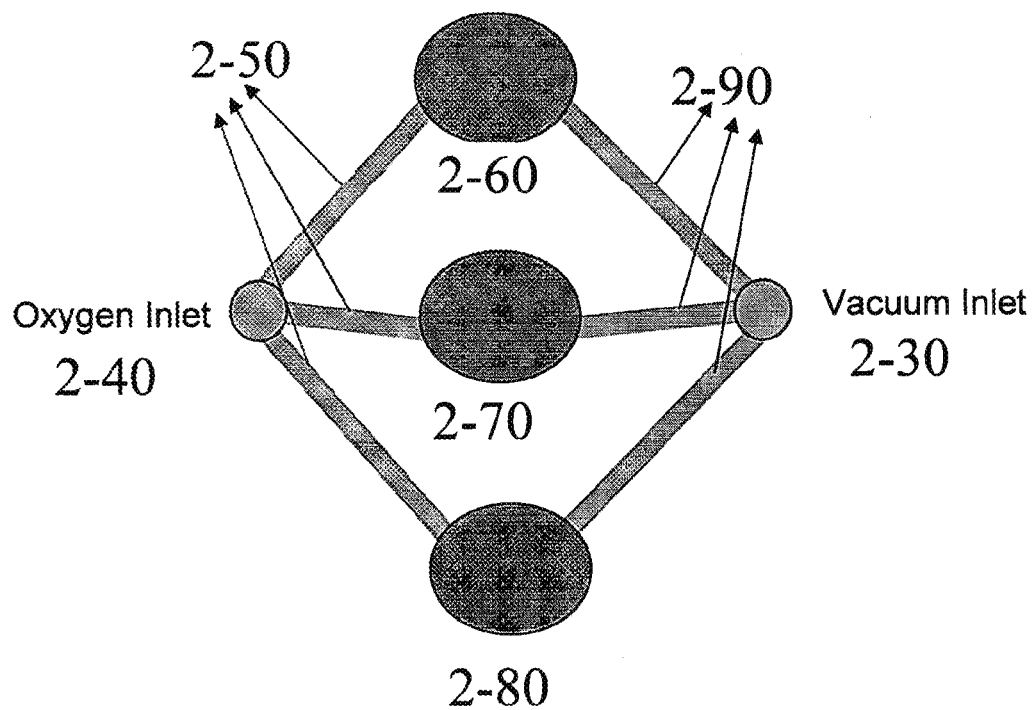
FIG. 2B depicts another embodied wound healing system, where multiple dressings (2-60, 2-70 and 2-80) are connected to a single oxygen and negative pressure source, respectively.

FIG. 2B depicts another embodiment of a device/method of this invention, where multiple dressings, as shown here for example, three dressings (2-60, 2-70 and 2-80, respectively) may be infused with oxygen and negative pressure is applied to each dressing, wherein a single oxygen source (2-40) and source of negative pressure (2-30) is utilized for each of a series of dressings. In this embodiment, tubing (2-50) connects the respective dressings to the oxygen source, or the tubing (2-90) connects the respective dressings to a source of negative pressure.

Figure 2C:
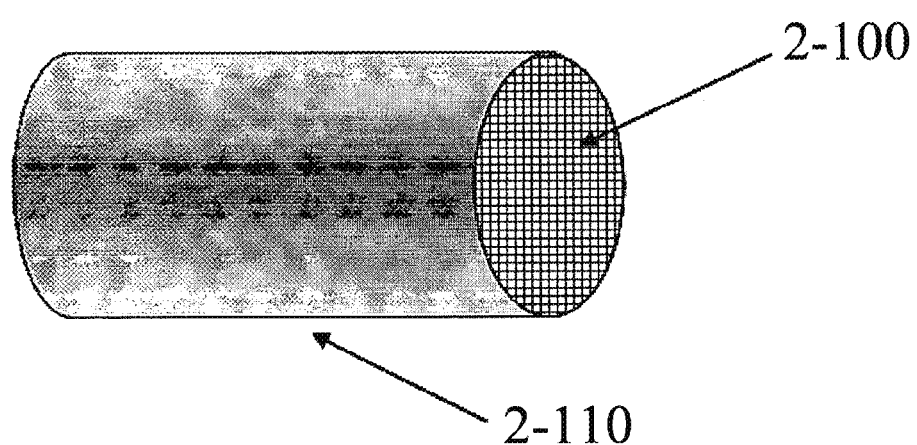
FIG. 2C provides an embodiment of tubing which may be used to convey oxygen to the wound, or convey fluid from the wound, or serve as a means for the application of negative pressure.

FIG. 2C depicts an embodiment of a material used to convey oxygen to the sound site or for the application of negative pressure. For such purpose, any tubing may be used, as described herein. In some embodiments, the tubing will comprise a sponge (2-100) surrounded by an air-tight drape (2-110), which tubing is flexible and unlikely to cause inflammation or discomfort when used on subjects for whom application of the devices and methods of this invention is desired.

Figure 3:
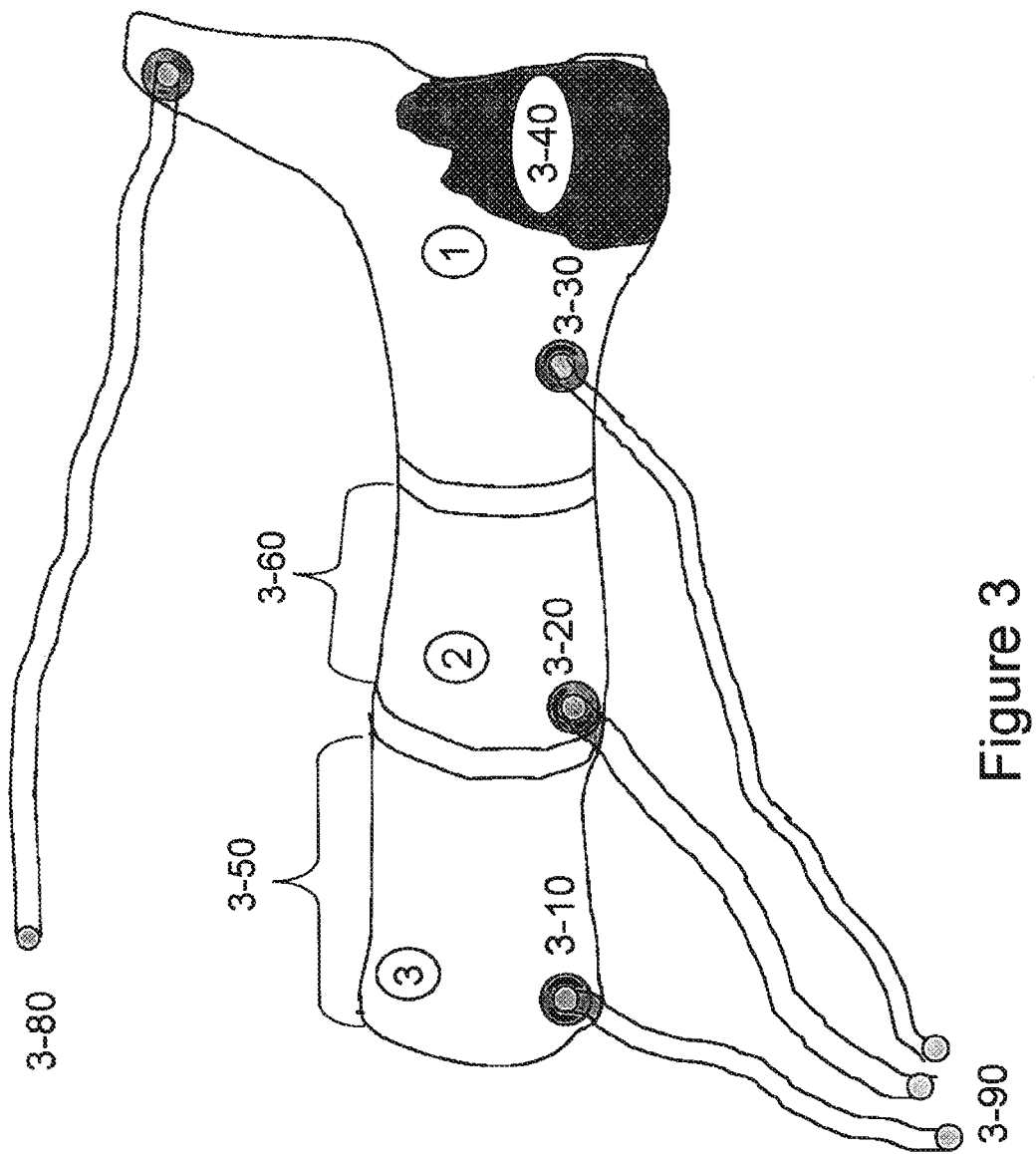
FIG. 3 presents an embodiment of a wound healing system of this invention, which includes a segmental dressing, i.e. a dressing which is divided into segments (3-50 and 3-60) and multiple inlets for the application of negative pressure (3-10, 3-20 and 3-30) connected to a source of negative pressure (3-90) and an inlet (3-100) for the application of oxygen (3-80), distal to the site at which negative pressure is applied, in the segment applied over the wound (3-40).

In FIG. 3, one embodiment of the of the dressing is shown with multiple inlets (3-10, 3-20, 3-30) for the application of negative pressure via the operational connection of the inlets to the source of negative pressure (3-90). The inlets are inserted in segments of the dressing which are separated one of the other by a gas and fluid impermeable barrier (3-50, 3-60). An oxygen inlet (3-80) is positioned distally to said multiple inlets (3-10, 3-20, 3-30) and within the compartment containing an open wound. The remaining compartments proximal to said wound-containing compartment allow for the controlled application of negative pressure, which pressure is less than the blood pressure detected within the wound-containing limb. Such pressure may be alternating or concurrent with application of negative pressure to the wound-containing compartment and allows promotion of healing of the wound.

Figure 4A:
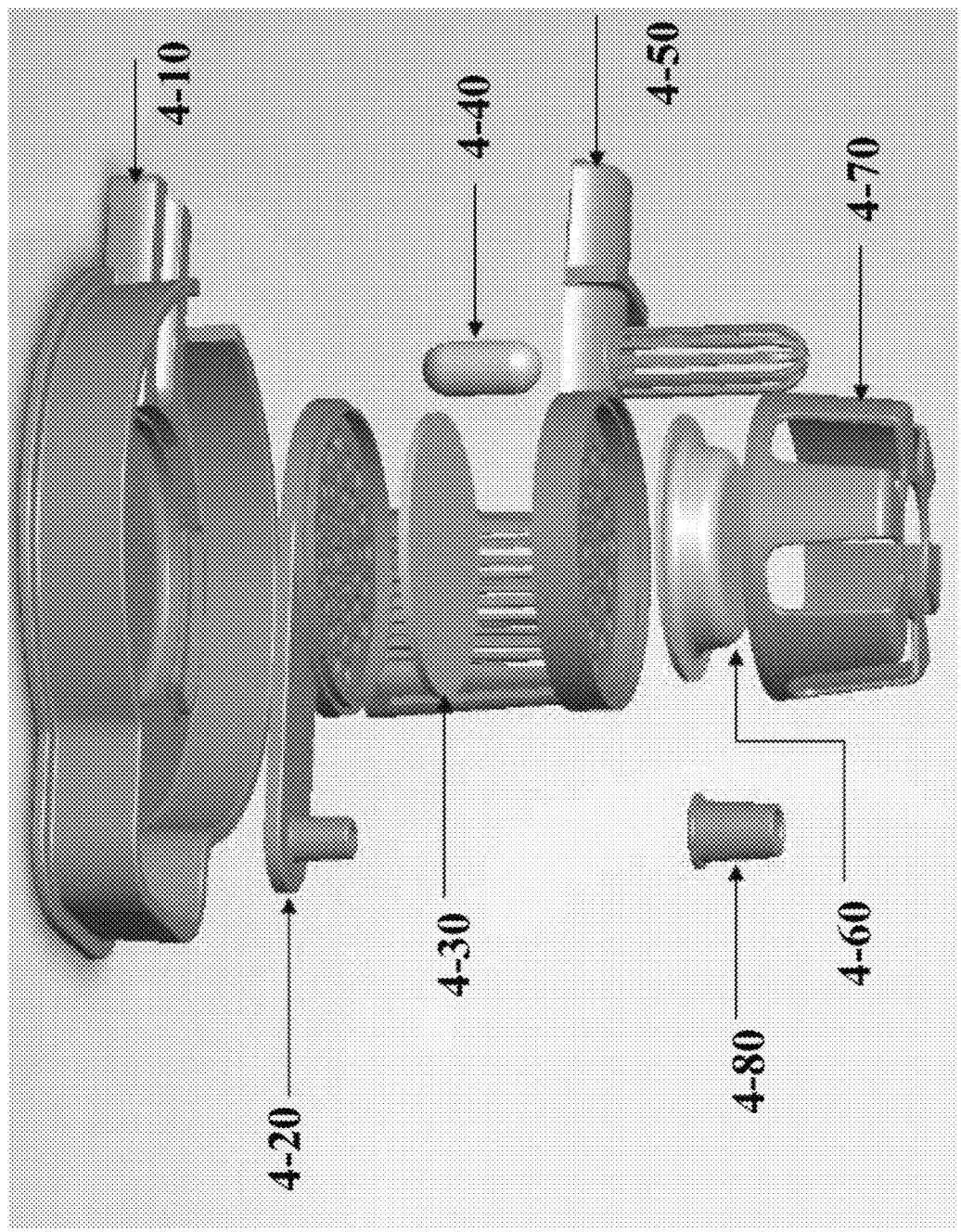
FIG. 4A depicts an embodiment of a cap for a fluid trap for use with the systems of this invention, containing multiple parts. A buoy 4-60 is contained within a net 4-70, serving as an indicator of fluid height within the trap. Secondary buoys 4-40, may be similarly contained within a bottle cover bottom 4-50, indicating fluid height. A filter 4-30 may be positioned above the bottle cover bottom to prevent contamination of the source of negative pressure, which filter is positioned below the bottle net 4-20 placed immediately under the bottle cap 4-10, forming a closed system. A silicone hat 4-80 may be used to ensure appropriate positioning of the bottle cap parts within the cap.
Figure 4B:
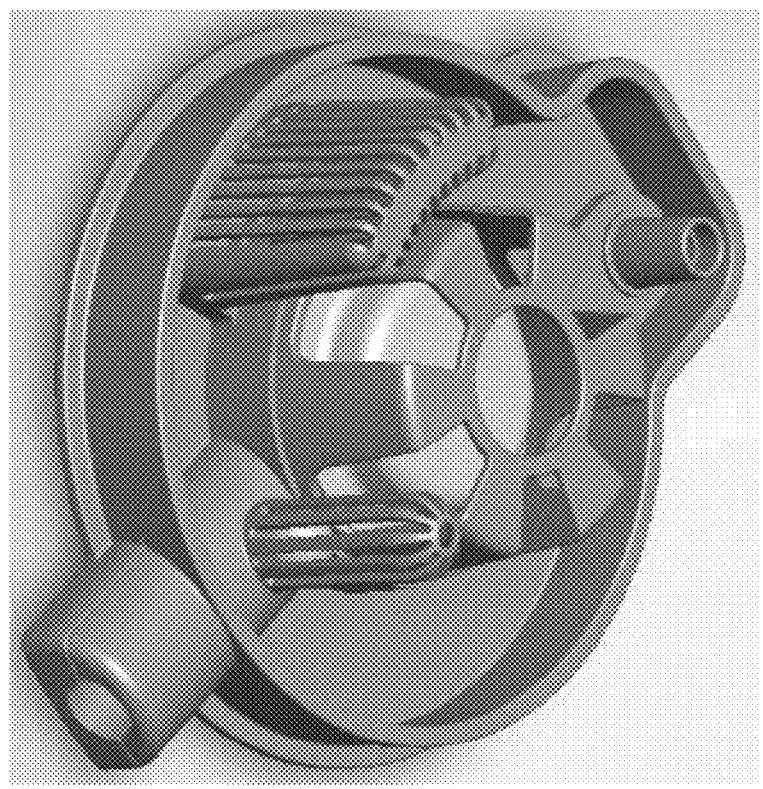
FIG. 4B depicts the assembled form of the bottle cap in FIG. 4A.
Figure 4C:
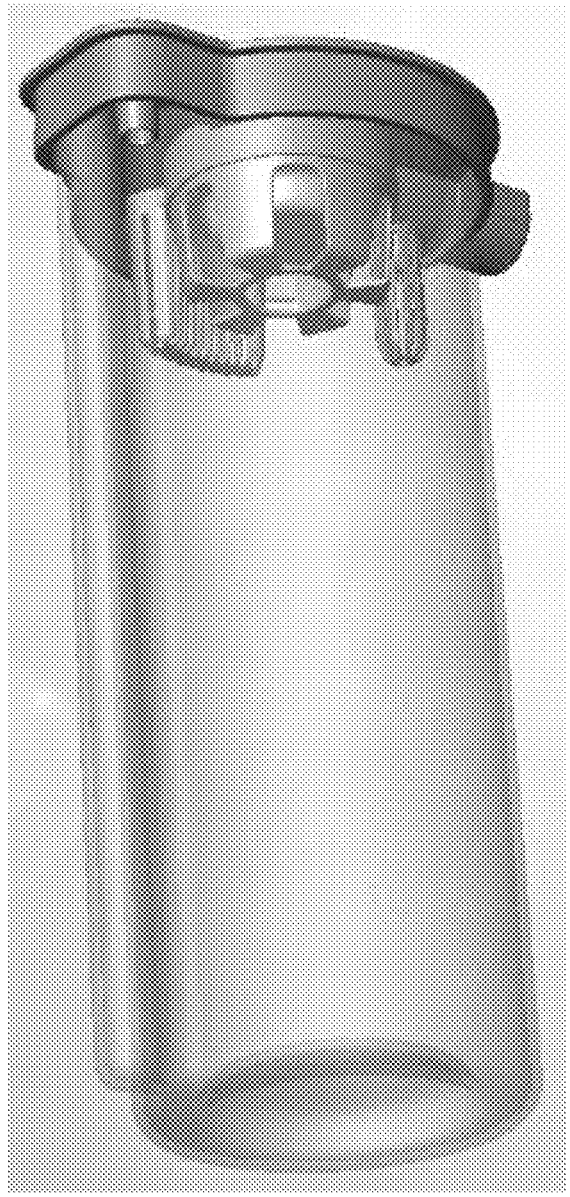
FIG. 4C depicts the assembled cap and fluid trap container.

FIG. 4(A-C) depicts an embodiment of a fluid-trap which can be used with the system of this invention. FIG. 4A depicts an embodiment of a cap for a fluid trap for use with the systems of this invention, containing multiple parts. A buoy 4-60 is contained within a net 4-70, serving as an indicator of fluid height within the trap. In some embodiments, a sensor relay system detects raising of the buoy and relays a signal to a controller regulating the application of negative pressure, which halts application of the negative pressure to the dressing. The trap system may comprise a secondary buoy 4-40, which is similarly contained within a bottle cover bottom 4-50, which in turn serves as a primary indicator of fluid height, which may be operationally connected to a sensor relay system as described above. A filter 4-30 may be positioned above the bottle cover bottom to prevent contamination of the source of negative pressure, which filter is positioned below the bottle net 4-20 placed immediately under the bottle cap 4-10, forming a closed system. A silicone hat 4-80 may be used to ensure appropriate positioning of the bottle cap parts within the cap.

This invention further provides a method for treatment of wounds comprising a dressing for wound containment which allows the application of negative pressure to the wounded area and the concurrent or temporal application of oxygen to the wound. Examples of wounds that require such treatment are crush injuries, lacerations, burns, infected wounds or a diabetes-associated wound complication. In some embodiments, during the treatment for the wound, skin grafts or flaps may be required for the process of healing. In some embodiments, application of the dressing on the wounded area after skin graft would be beneficial for the healing process. In some embodiments the dressing may comprise of several layers which are placed on top of the wound to accommodate the surface of the wounded area. In some embodiments, the dressing is comprised from a sponge that allows the absorption of the wound exudates and the application of negative pressure which support the removal of wound fluids and contamination from the wounded area. In some embodiments, whether the dressing is comprised of bandages or sponges, the composition of the dressing material is compressible to allow the application of pressure to secure skin graft to its place. In some embodiments, the sponge is a combined layer sponge, where the first layer proximal to the wound is absorptive and the second layer distal to the wound is gas and fluid impermeable. Furthermore, the dressing material is elastic to allow covering of the wounded area. In some embodiments, application of negative pressure requires the addition of an impermeable outer layer on top of the absorbent layers of the dressing to accommodate a tight occlusion around the wounded area. In this method the therapeutic application of negative pressure is done by connecting the dressing to a negative pressure source. In some embodiments, this connection is done through an inlet in the dressing. In some embodiments of this method, the negative pressure is applied to sections of the dressing, where these sections are separated by a gas and fluid impermeable barrier within the dressing. This allows the application of negative pressure to parts of the wound as directed by the treatment administer. Negative pressure promotes the healing of wound through multiple pathways including removal of excess fluids from the wound, increased blood circulation at the site of the wound, decreasing the bacterial load on the wound, increasing growth factors and increasing white blood cells and fibroblast at the site of the wound. In some embodiments, negative pressure is applied to the wound through the dressing at a range of 20 mmHg to 500 mmHg. In some embodiments, the negative pressure would be higher than 200 mmHg, for short periods of time, in order to facilitate fast and efficient removal of toxic fluids or materials from the wound. In some embodiments, the negative pressure and/or oxygen flow is adjustable using a regulator and/or synchronizing system, thus enabling the determination of the amount of negative pressure and/or $pO_2$ at the site of the wound. In some embodiments, a pressure sensor inside the wound dressing indicates the negative pressure's induced static pressure on the wound or limb that may interfere or obstruct blood flow distally, allowing the adjustment to be made by using said regulator. In some embodiments, a fluid trap is disposed "in-line" between the negative pressure source and the dressing. The fluid trap retains wound fluids draw from the wound by the application of negative pressure. In some embodiments a sensor is built into the trap for detection of fluid levels and fluid composition. During the treatment the sensor, in some embodiments, indicates when the fluid trap is full and operates a relay for shutting down the negative pressure source and oxygen flow. In some embodiments, the sensor may also monitor excess blood in the wound fluids by monitoring fluid composition. When excess blood (over a predetermined threshold) is detected the sensor, for example, through a relay, for example as described in U.S. Pat. No. 5,411,269 shuts down the negative pressure source and alerts the care givers by and indicative light and/or sound.

In treatment of wounds due to infection of anaerobic bacteria application of oxygen to the wounded site in parallel to negative pressure has an advantage in creating an oxygenated environment that restricts or may terminate the growth and proliferation of anaerobe bacteria.

In some embodiments, this invention is aimed at treating wounds resulting from crush injuries, lacerations, burns, infections and diabetes-associated complications, and the like.

In one embodiment, this invention provides a method of treating a wound in a subject, said method comprising the steps of applying a source of oxygen containing to a wound in said subject and concurrently applying negative pressure to said wound, wherein said source of oxygen maintains oxygen at a value of at least 21% of the total gas in said source and whereby application of oxygen and negative pressure to said wound stimulates wound healing.

In one embodiment, this invention provides a method of treating or preventing anaerobic infection of a wound in a subject, said method comprising the steps of applying a source of oxygen containing to a wound in said subject and concurrently applying negative pressure to said wound, wherein said source of oxygen maintains oxygen at a value of at least 21% of the total gas in said source and whereby application of oxygen and negative pressure to said wound treats or prevents anaerobic infection of said wound.

In some embodiments, the methods of this invention make use of the devices as herein described. In some embodiments, the methods of this invention may comprise administering a therapeutic agent to the subject prior to, concurrent with or following the carrying out of the described elements of the methods of this invention, as herein described.

In some embodiments, therapeutic medicaments are administered in parallel to effecting the methods of this invention, i.e. wound treatment with combined negative pressure and oxygen application. This is done, in one embodiment, by administering these medicaments to the patient or by applying the medicaments onto the dressing of the wound. The medicaments, in some embodiments, may include, but are not limited to, antiseptics, antibiotics, enzymes, analgesic drugs and anti-inflammatory drugs. Administration of wound medicaments of the invention can include local or systemic administration, including injection, oral administration, or catheterized administration, and topical administration. For treatment of wounds on the surface of the body, a wound healing composition is typically prepared in a topical form, either as a liquid solution, suspension, gel, cream or chemically attached to the dressing to be slowly released to the wound. However, solid forms suitable for solution or suspension in liquid vehicles prior to injection can also be prepared, for local treatment of deep wounds or by continuous or intermittent catheterized administration of medicaments into deep wounds or cavities (as for treatment of infected pacemakers or other indwelling devices). Both the dose of a particular wound healing composition and the means of administering the composition can be determined based on specific qualities of the wound healing composition, the condition, age, and weight of the patient, the type and extent of the wound being treated, the device being treated and other relevant factors. In some embodiments, wound healing medicaments can comprise a pharmaceutically acceptable carrier. Pharmaceutically acceptable carriers are well known to those in the art.

Such carriers include, but are not limited to, large, slowly metabolized macromolecules, such as proteins, polysaccharides, polylactic acids, polyglycolic acids, polymeric amino acids, amino acid copolymers, and inactive virus particles. In one embodiment, parallel application of negative pressure through an inlet in the dressing and inflow of oxygen through another distal inlet results in a synergistic outcome of faster healing. In some embodiments, intermitted application of oxygen or negative pressure or both may result in better healing of the infected wound.

Figure 5A:
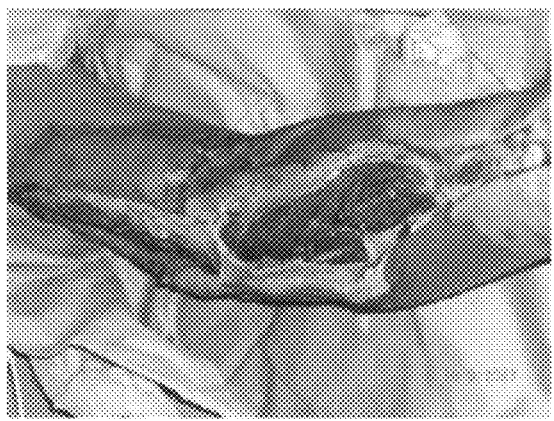
FIGS. 5A, 5B and 5C present photographs of skin lesions of a subject with necrotizing facsiitis in an upper limb before, during and after treatment according to an embodiment of a method of this invention.
Figure 5B:
Figure 5C:
Figure 6A:
FIGS. 6A, 6B, and 6C present photographs of skin lesions of another subject with diabetic related wounds, before, during and after treatment according to an embodiment of a method of this invention.
Figure 6B:
Figure 6C:
Figure 7A:
FIGS. 7A, 7B and 7C present photographs of skin lesions of another subject having burns, before, during and after treatment according to embodiment of a method of this invention.
Figure 7B:
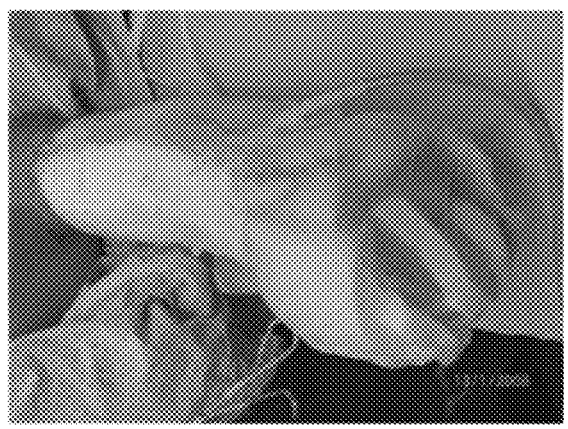
Figure 7C:

Referring now to FIGS. 5A to 5C, 6A to 6C, and 7A to 7C where application of a makeshift device similar in principle of operation to that described in FIG. 1 for treatment of wounds are shown. In FIGS. 5A to 5C, a 49-year-old male, suffering from sepsis and necrotizing fasciitis is treated with regulated oxygen-negative pressure therapy (RO-NPT). This patient required mechanical ventilation; therefore the placement of the patient in a hyperbaric oxygen chamber was not possible. FIG. 5B presents a photograph of one embodiment of the makeshift system used in treating the wound. Once the patient was exposed to RO-NPT therapy, the wounds began healing. FIG. 5C presents a photograph showing extinction of infection and resolution of the wound which occurred within a period of 4 weeks. In FIGS. 6A to 6C, a 66-year-old diabetic female presented with severe signs of sepsis and necrotizing fasciitis due to complications of diabetes. Photographs of the wounds prior to treatment are presented in FIG. 6A showing necrotizing fasciitis in the deep tissue along the fascia involving the right inguinal region, the medial and lateral thigh and along the medial aspect of the right lower limb down to the ankle. FIG. 6B presents a photograph of one embodiment of the makeshift system for RO-NPT treatment. After treatment substantial improvement was achieved as shown in FIG. 6C. FIGS. 7A to 7C show a 36-year-old male sustained a crash and deep burn injury of the Lt. fore-arm and elbow, presented with deep 2nd-3rd degree burns. Photographs of the wounds prior to treatment are presented in FIG. 7A. FIG. 7B presents a photograph of one embodiment of the makeshift system used to treat the patient. Upon RO-NPT treatment and skin grafts substantial improvement was achieved as shown in FIG. 7C.

Necrotizing soft-tissue infection is a severe type of tissue infection that can involve the skin, subcutaneous fat, the muscle sheath (fascia), and the muscle. It can cause gangrene, tissue death, systemic disease and death. Powerful, broad-spectrum antibiotics must be given immediately through a vein (IV) in an attempt to control the infection by quickly raising the blood levels of the antibiotic. Surgery is required to open and drain infected areas and remove dead tissue. Skin grafts may be required after the infection is cleared. If the infection is in a limb and cannot be contained or controlled, amputation of the limb is a typical outcome. If the organism is determined to be an oxygen-avoiding bacterium (anaerobe), the patient may be placed in a hyperbaric oxygen chamber, a device in which the patient is given 100% oxygen at several atmospheres of pressure. The outcomes are variable. The type of infecting organism, rate of spread, susceptibility to antibiotics, patient's general health condition, the availability of treatment facilities (as hyperbaric chamber) and the timing of diagnosis all contribute to the final outcome. Scarring and deformity are common with this type of disease. Fatalities are high even with aggressive treatment and powerful antibiotics. Untreated, the infection invariably spreads and causes death. It would be contraindicated to seal NF wounds, and preclude access of air to the wound site, which is precisely what occurs in RNPT treatment of NF wounds that even actively reduce $pO_2$ in the wound atmosphere. The methods/devices/systems of this invention uniquely offer a clear advantage for the treatment of such wounds.

In some embodiments, the invention provides methods for treating wounds using the devices and systems of this invention.

In some embodiments, such methods comprise placing a wound in subject within a wound healing system or device of this invention, applying negative pressure to the wound via the devices and/or systems of the invention and concurrently or temporally applying oxygen to the devices and/or systems of the invention, whereby simultaneous application of oxygen and negative pressure to the wound stimulates wound healing.

In some embodiments of the invention, according to this aspect, treatment may further comprise making use of a system including any embodiment listed herein. In some embodiments, such systems may comprise a dressing comprised of a first layer, which is gas and fluid permeable having a plurality of discrete oxygen passageways overlying the wound and through which negative pressure established by the negative pressure source is communicated to the wound. In some embodiments, the method may further comprise administering an antiseptic, antibiotic, analgesic, or an anti-inflammatory medicament to said subject, or in some embodiments, the method may make use of a dressing, which incorporates an antiseptic, antibiotic, analgesic, or an anti-inflammatory medicament.

In some embodiments, the wound treated by the methods of this invention or treated with the systems and/or devices of this invention is a result of a trauma (burn, laceration), an infection, PVD or a diabetes-associated complication.

In some embodiments, the infection is caused by an anaerobic or facultative anaerobic organism. In some embodiments, treatments of this invention may include treatment of infection with *Clostridium, Actinomyces, Streptococcus, Staphylococcus, Escherichia, Bacteriodes, Peptococcus, Fusobacterium, Arachnia, Eubacterium, Bifidobacterium, Lactobacillus, Propionibacterium, Peptostreptococcus, Veillonella, Acidominococcus, Pseudomonas, Prevotella, Porphyromonas, Gemella, Bacillus* and others.

Anaerobes are the predominant fraction of normal human skin and mucous bacterial flora, and are consequently a common cause of endogenous infection. In situations such as trauma, vascular occlusion or surgical manifestations when oxygen concentration is reduced in tissue, indigenous anaerobic flora multiply quickly and often result in aggressive infection and sepsis.

Biofilms appear to be more abundant in chronic wounds, with diverse polymicrobial communities including strictly anaerobic bacteria being common in wound sites. Moreover, in wound sites comprising mixed infections, the presence of aerobic or facultative aerobes provides a habitat which supports growth of anaerobes by reducing the oxygen concentration in the infected tissue. This fact may even be of higher significance in the sealed environment of RNPT, or when systems are sealed but negative pressure is not properly applied. RNPT is therefore contraindicated in frank anaerobic infections or when growth of anaerobic infection is suspected.

The methods/devices and systems of this invention are particularly useful for treatment of wounds infected with anaerobic organisms. The current recommended treatment for anaerobic infection, for example, in necrotizing fasciitis includes the immediate administration of wide spectrum antibiotics, urgent, aggressive, frequent, surgical intervention and supplementation of high local and systemic levels of oxygen as in hyperbaric oxygen treatment (HBO). The global availability of HBO facilities is limited, its costs are high and treatment may be restricted in various clinical conditions (for example, in non-ambulatory patient care).

RO-NPT is a cost-effective treatment applying readily accessible technologies that can be used for the treatment of various wounds, such as necrotizing fasciitis, acute trauma, diabetic and PVD affected feet and for complicated acute and chronic wounds. RO-NPT can be employed either in a hospital or as a home care treatment, and can be utilized on a large scale under disaster conditions, field settings and other scenarios where surgical and other therapeutic conditions may not be readily available or feasible.

The devices/systems of this invention may be applied to therapy of most wounds, and is useful, in some embodiments, in particular for the treatment of soft tissue and bone infections.

While various embodiments of the present invention have been presented, it is possible to use various alternatives, modifications and equivalents. It is to be understood that any feature described herein, may be combined with any other feature described herein. It is to be understood that the article "a", or "an" refers to a quantity of one or more of the item following the article, except where expressly stated otherwise.

The following examples are intended to illustrate but not limit the present invention.

EXAMPLES

Example 1

Application of Henry's Law

The partial pressure of a gas in a mixture of ideal gases is defined as the pressure which the gas would have if it alone occupied the volume. The total pressure of a gas mixture is the sum of the partial pressures of each individual gas in the mixture. The partial pressure of a gas dissolved in a liquid is the partial pressure of that gas which would be generated in a gas phase in equilibrium with the liquid at the same temperature. The partial pressure of a gas is a measure of thermodynamic activity of the gas's molecules. Gases will always flow from a region of higher partial pressure to one of lower pressure; the larger this difference, the faster the flow. Gases dissolve, diffuse, and react according to their partial pressures, and not necessarily according to their concentrations in a gas mixture.

The solubility of a gas in a liquid solution is affected by temperature and by the partial pressure of that gas over the liquid as was formulated by William Henry in the early 17th century. In Henry's law; the solubility of a given gas dissolved in a given type and volume of a liquid, at a constant temperature, is directly proportional to the partial pressure of that gas, in the overlying atmosphere, in equilibrium with that liquid. And when applied to the solubility of Oxygen in water:

$$pO_2 = KO_2 XO_2$$

where $pO_2$ is the partial pressure of oxygen in Torr, $XO_2$ is the mole fraction of oxygen in oxygen-saturated water, and $KO_2$ is the equilibrium constant for oxygen in water (about $3.30 \times 10^7$ K/Torr when gas is dissolved in water at 298 Kelvin). High humidity lowers very slightly the fraction of oxygen in the air, and so, saturated dissolved oxygen levels are lowered slightly. Many empirical equations are available to accurately estimate oxygen solubility as a function of temperature, pressure, and humidity. The more accuracy required the more complex the equations.

Based on Henry's Law, lower air pressure, as found in the air atmosphere of wounds treated with regulated negative pressure-assisted wound therapy (RNPT) necessarily result in lower $pO_2$ levels in the wound site. Thus, the fluid within the wound treated with RNPT, according to Henry's law would necessarily contain less dissolved oxygen than untreated wounds. In the closed, moist milieu of a vacuum treated wound, when the wound is already contaminated, an ideal microenvironment for anaerobes then arises, owing to the diminished $pO_2$. This provides an optimal environment for the development of anaerobic infections.

Example 2

Application of an Embodied Device of this Invention

An in-vitro model was designed, to assess oxygen behavior in a simulated wound atmosphere. An experimental setup was planed to determine the spectrum levels of oxygen partial pressures in the environment of wounds treated with RNPT and RNPT simultaneously enriched with oxygen under various oxygen flow conditions and varied application of negative pressure.

Figure 8A:
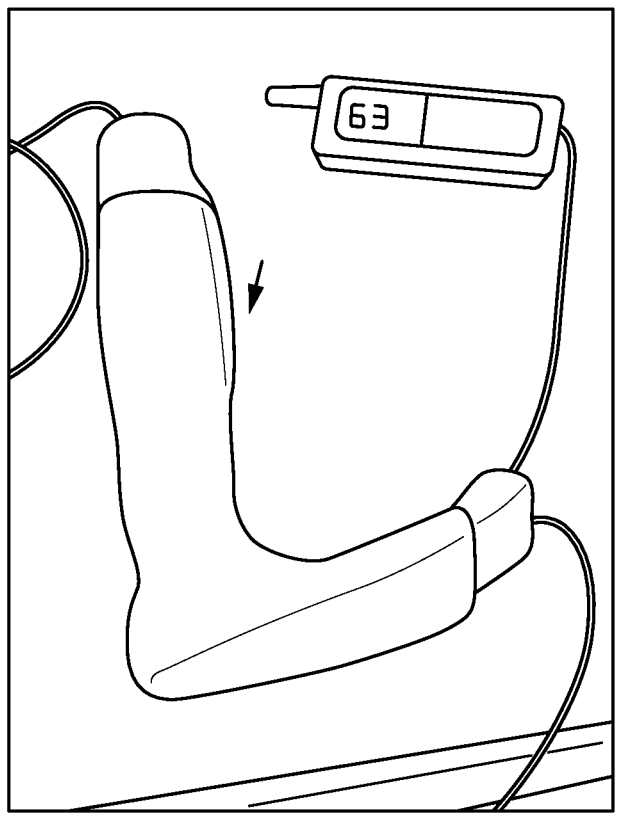
FIGS. 8A and 8B present photographs of the experimental setup to determine oxygen levels of wound sites using a phantom leg. RNPT systems were evaluated in a side-by-side comparison study with embodiments of RO-NPT systems of this invention. A. circumferential dressing of leg by a sponge sealed entirely by a drape B. inlet of oxygen flow. C. vacuum outflow insert. D. oxygen sensor at the vacuum outflow. E. $pO_2$ detector.
Figure 8B:
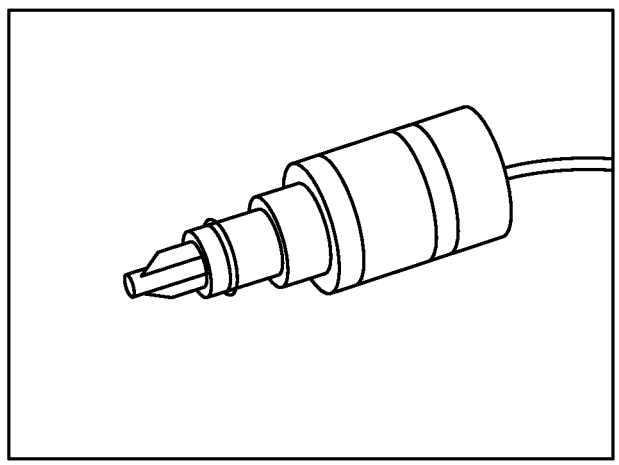

The system utilized is depicted in FIGS. 8A to 8B. The system combines application of a regulated oxygen-enriched atmosphere with RNPT. A phantom leg was circumferentially draped with Polyvinyl chloride (IUPAC Polychloroethene) foam and was sealed under a drape covering the entire treated area. The system affords a relatively large volume cavity, necessitating a high flow vacuum pump to accommodate the cavity volume and the high inflow volume of oxygen, easily achieved by connecting the apparatus to a wall suction outlet as a sub atmospheric source.

Negative pressure was applied to the system via use of a Healer a (iLSino Ltd. Taiyuan, PRC) operating in external sub atmospheric source mode set to levels typically applied in clinical cases (in the range of 50-200 mmHg in 25-50 mmHg increments). Oxygen flow was controlled and delivered to the simulated wound by an oxygen regulator (Silbermann Technologies Ltd. Petah-Tikva, Israel) through a micro filter in predetermined 1 liter per minute flow increments in a range of 1 to 10 liters per minute. 100% medical oxygen was administered to the counter edge of the vacuum source so that oxygen flow was homogenously distributed through the sponge cavities, in contact with the wound, over the entire wound surface area and was sealed by a drape. Pressure was readjusted following the administration of oxygen to the system. $pO_2$ in the wound atmosphere was continuously monitored by a $pO_2$ detector (Teledyme Electronic Devices, City of Industry Calif., USA). Calibration was performed at room atmosphere and 100% $pO_2$ prior to initiation of each of the experimental set. The probe was positioned at the outflow suction port and $pO_2$ was recorded after equilibration was reached. Considering the internal $pO_2$ sensor chamber structure, limited ventilation of the sensor was expected especially in the low oxygen flow range thus, the detected levels of $pO_2$ represent a minimum in terms of the actual levels of oxygen present in the system.

Figure 9:
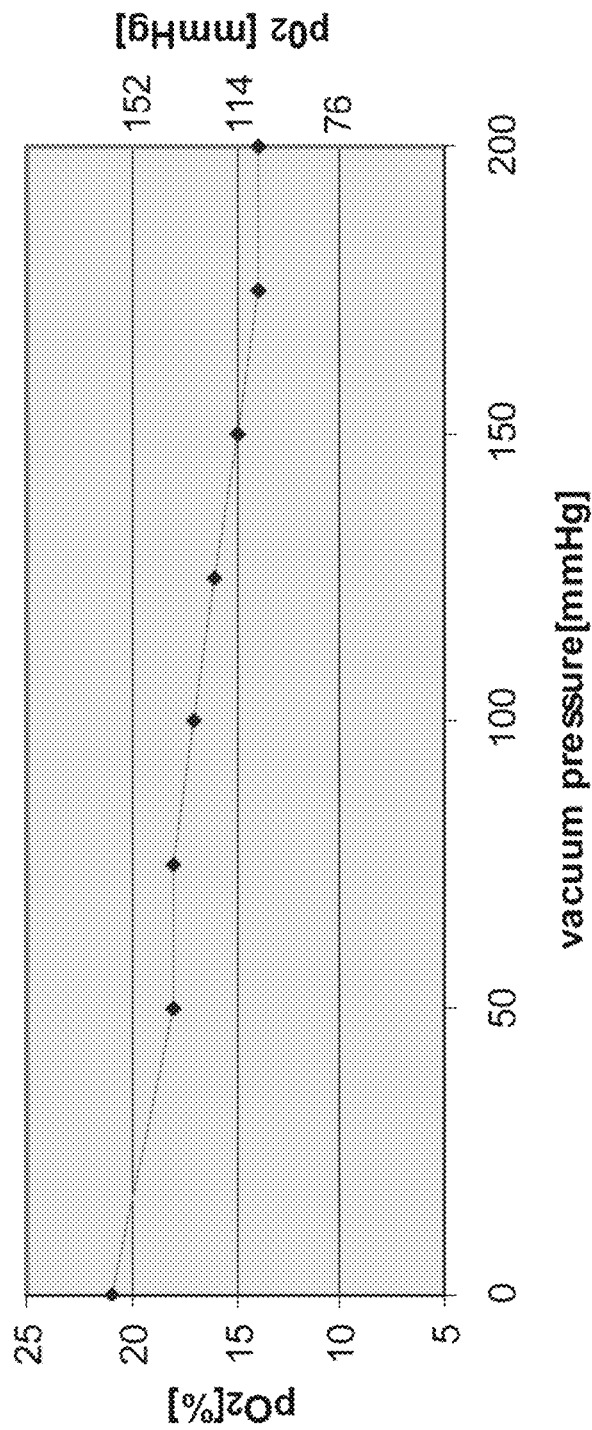
FIG. 9 depicts reduced $pO_2$ values in a simulated wound atmosphere at various clinical RNPT vacuum pressure level ranges, where no supplemental oxygen is provided.

$PO_2$ values were recorded in relative percent units following calibration of the sensor detecting the oxygen concentration under atmospheric conditions and in an environment of 100% oxygen, at sea level pressure. $pO_2$ concentration in an environment subjected to RNPT decreased to values below the 21% atmospheric $pO_2$ level (FIG. 9). A reverse correlation with sub atmospheric pressure applied to the simulated wound was seen, such that $PO_2$ reached its minimum value (down to 14 mmHg) at the highest RNPT pressure setting evaluated (200 mmHg).

Figure 10:
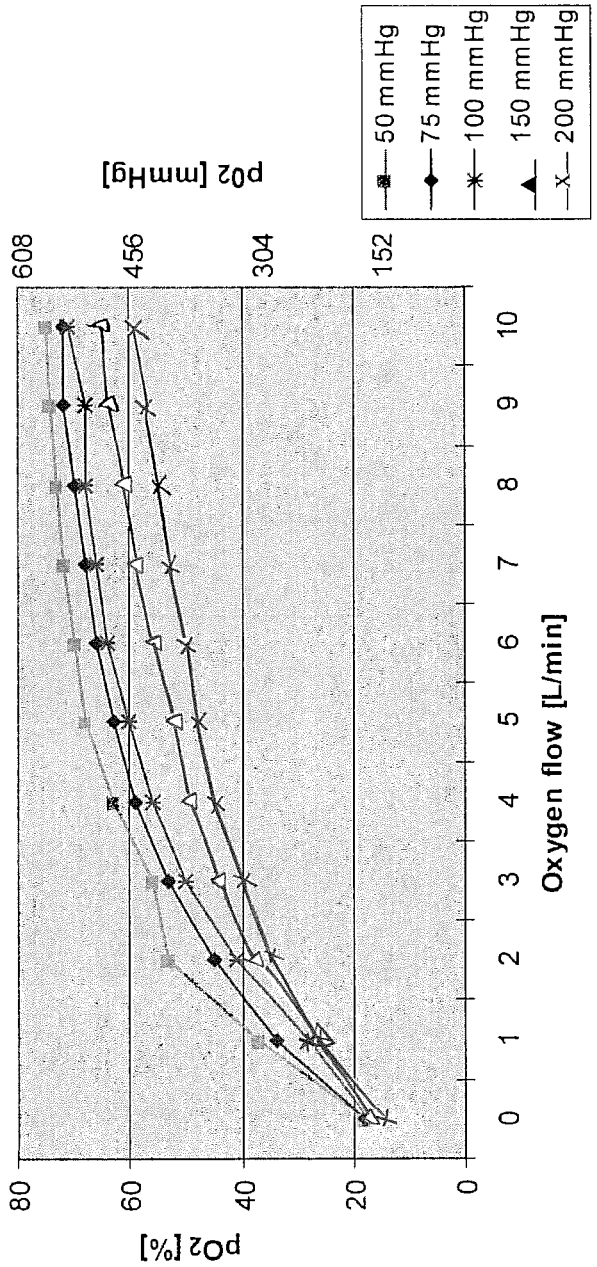
FIG. 10 depicts the measured $pO_2$ values at various clinically relevant oxygen flows and sub atmospheric pressure range.

In marked contrast, simultaneous administration of oxygen and negative pressure, afforded by the RO-NPT devices of this invention increased $pO_2$ concentration at the simulated wound site (FIG. 10), with applied sub atmospheric pressure correlating with oxygen flow. $pO_2$ values reached a maximum value close to 80% under relatively low sub atmospheric pressure (50 mmHg) under high Oxygen flow (10 liters/min), representing an up to four-fold increase over baseline [no-oxygen inflow, and sub atmospheric pressure state].

The solubility of oxygen in fluid solutions is roughly proportional to the partial pressure of oxygen in the surrounding atmosphere. In low air pressures as in the air atmosphere of wounds treated with RNPT, $pO_2$ is expected to be lower than 21%, meaning lower solubility of oxygen in the wound fluids. In this Example, $pO_2$ measurements in a simulated wound atmosphere without supplemental oxygen were in the range of 18-14 mmHg for sub atmospheric pressures of 50-200, respectively, indicating that the higher the sub atmospheric pressure applied, the lower the $pO_2$ concentration at the wound site, rendering the wound site more susceptible for infection, in particular with anaerobic flora.

Increasing wound atmospheric $pO_2$ would lead to increased oxygen solubility in the wound's fluid thus reducing or eliminating the chance for anaerobic infections.

Example 3

Peripheral arterial disease (PAD) causing arterial insufficiency is the most important factor relating to the outcome of a diabetic foot ulcer. The prevalence of PAD in people with diabetes is probably high, and ranges from 10% to 40% depending on the definition used; in patients with foot ulcers approximately 50% have signs of PAD.

Critical ischemia indicates risk of amputation of a major part of the limb. Chronic critical ischemia is currently defined by either of the two following criteria: persistent ischemic rest pain requiring regular analgesia for more than two weeks; ulceration or gangrene of the foot or toes—both associated with an ankle systolic pressure of <50 mmHg or a toe systolic pressure of <30-50 mmHg. The most widely used method for the diagnosis and quantification of PAD is the measurement of ankle pressure.

The external application of a vacuum dressing in such patients, however, may cause perfusion impairment of the distal limbs due to the pressure from the dressing garment.

When the peripheral blood pressure within the limb is lower than the internal pressure generated by the applied vacuum on the circumferential sponge dressing, it can worsen the ischemic condition and induce necrosis.

While the disclosure has been illustrated and described, it is not intended to be limited to the details shown, since various modifications and substitutions can be made without departing in any way from the spirit of the present disclosure. As such, further modifications and equivalents of the invention herein disclosed can occur to persons skilled in the art using no more than routine experimentation, and all such modifications and equivalents are believed to be within the spirit and scope of the disclosure as defined by the following claims.

What is claimed is:

1. A wound healing system, comprising:
   a dressing for wound containment comprising:
   a first inlet, wherein the first inlet is operationally connected to a source for the application of negative pressure to a wound covered by the dressing;
   a second set of inlets suitable for application of gaseous oxygen therethrough, wherein the second set of inlets are located most distally from the first inlet along one or more Cartesian axes and wherein the second set of inlets are operationally connected, independently from the source for the application of negative pressure, to a source for the application of gaseous oxygen, which conducts gaseous oxygen to a wound covered by the dressing, and wherein the negative pressure and gaseous oxygen are applied at most distal sides with respect to each other along one or more Cartesian axes;
   a controller configured to regulate the application of negative pressure from the source, and to apply the negative pressure along a different Cartesian axis other than a Cartesian axis along which the gaseous oxygen is applied, wherein the negative pressure and the gaseous oxygen are applied within a same compartment containing the open wound;
   a first regulator for the source for the application of negative pressure to supply 20-500 mmHg of pressure;
   a second regulator for the source for the application of gaseous oxygen to maintain wound atmospheric oxygen at a value of at least 21% of the total gas supplied by said source, wherein the negative pressure and the value of oxygen provide an oxygenated environment to restrict growth of anaerobe bacteria; and
   a fluid trap operationally connected to the first inlet and to the source for the application of negative pressure, such that fluid from the wound covered by the dressing is conveyed to the fluid trap,
   wherein the fluid trap comprises a detector moiety which senses a change in fluid characteristics in the trap and regulates the application of negative pressure in response thereto, wherein the change in fluid characteristics includes detection of blood level exceeding a pre-set level in the fluid conveyed from the wound.

2. The system of claim 1, wherein the dressing is compressible, elastic or a combination thereof.

3. The system of claim 1, wherein the dressing is of a dimension which accommodates the area of the wound and cavity.

4. The system of claim 1, wherein the dressing is fluid permeable.

5. The system of claim 4, wherein the dressing comprises a first and second layer, wherein the second layer comprises a gas or fluid impermeable material.

6. The system of claim 5, wherein the second layer comprises an indicator that is distinguishable upon application of negative pressure.

7. The system of claim 1, wherein the first regulator applies continuous or interrupted synchronized negative pressure.

8. The system of claim 1, wherein the first regulator comprises a valve which selectively applies negative pressure to individual inlets.

9. The system of claim 1, wherein the application of negative pressure is in an alternating or sequential manner.

10. The system of claim 1, wherein the fluid trap further comprises an access port for sampling wound fluids.

11. The system of claim 1, wherein the fluid trap further comprises a filter positioned between the fluid trap and the source for the application of negative pressure for preventing access of wound fluids to the source for the application of negative pressure.

12. The system of claim 1, wherein the first regulator is also for the application of negative pressure to supply 20-500 mmHg of pressure.

13. The system of claim 12, wherein the first regulator and second regulator apply oxygen and negative pressure in an alternating manner.

14. The system of claim 12, wherein the first regulator and second regulator apply oxygen and negative pressure in a concurrent manner.

15. The system of claim 1, further comprising a filter positioned between the source for the application of oxygen and the dressing, for prevention of contamination of the wound.

16. The system of claim 1, wherein the dressing further comprises an oxygen sensor.

17. The wound healing system of claim 1, further comprising:
- a first absorptive layer and a second impermeable layer; wherein the first layer is positioned proximal to the wound, and the second layer is distal to the wound and wherein the dressing is compartmentalized into sections, such that negative pressure is independently applied to each of the sections; and
- at least a second and third inlet operationally connected to a source for the application of negative pressure and operationally connected independently to the sections; whereby application of negative pressure to the dressing is unequal, such that a first portion of the dressing proximal to the second or third inlet is differentially subjected to negative pressure in comparison to a second portion of the dressing distal to the second or third inlet.

18. A method of treating a wound in a subject, the method comprising:
- applying the wound healing system of claim 1 to the wound such that the wound is substantially covered by the dressing;
- applying negative pressure to the first inlet in the dressing; and
- concurrently or temporally applying oxygen to the second inlet,
- wherein the applying oxygen to the second inlet comprises applying oxygen to the wound in the subject and applying the negative pressure to the first inlet comprises applying negative pressure to the wound, and wherein the source of oxygen maintains oxygen at a value of at least 21% of the total gas in the source and whereby application of oxygen and negative pressure to the wound stimulates wound healing.

19. A method of treating or preventing anaerobic infection of a wound in a subject, the method comprising:
- applying the wound healing system of claim 1 to a wound in a subject at risk for or suffering from an anaerobic infection of the wound, such that the wound is substantially covered by the dressing;
- applying negative pressure to the first inlet in the dressing; and
- concurrently or temporally applying oxygen to the second inlet,
- wherein the applying oxygen to the second inlet comprises applying oxygen to the wound in the subject and applying the negative pressure to the first inlet comprises applying negative pressure to the wound, and wherein the source of oxygen maintains oxygen at a value of at least 21% of the total gas in the source and whereby application of oxygen and negative pressure to the wound treats or prevents anaerobic infection of the wound.

20. The system of claim 1, wherein the dressing comprises a drape configured to deform upon the application of negative pressure so as to visually indicate the presence of the negative pressure.

* * * * *